US011153090B2

(12) United States Patent
Lee et al.

(10) Patent No.: US 11,153,090 B2
(45) Date of Patent: Oct. 19, 2021

(54) ELECTRONIC DEVICE AND METHOD FOR MANAGING BODY INFORMATION BY ELECTRONIC DEVICE

(71) Applicant: Samsung Electronics Co., Ltd., Gyeonggi-do (KR)

(72) Inventors: Seon-Hyung Lee, Gyeonggi-do (KR); Soon-Hwan Kwon, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 181 days.

(21) Appl. No.: 15/844,871

(22) Filed: Dec. 18, 2017

(65) Prior Publication Data

US 2018/0176019 A1 Jun. 21, 2018

(30) Foreign Application Priority Data

Dec. 19, 2016 (KR) .................. 10-2016-0173846

(51) Int. Cl.
*H04L 9/32* (2006.01)
*G06K 9/00* (2006.01)
*H04L 29/08* (2006.01)
*A61B 5/117* (2016.01)
*H04W 4/38* (2018.01)
(Continued)

(52) U.S. Cl.
CPC ............ *H04L 9/3231* (2013.01); *A61B 5/117* (2013.01); *A61B 5/4869* (2013.01); *G06K 9/00892* (2013.01); *G16H 15/00* (2018.01); *G16H 50/70* (2018.01); *H04L 67/2842* (2013.01); *H04L 67/306* (2013.01); *H04W 4/38* (2018.02)

(58) Field of Classification Search
USPC ........ 713/186, 150, 163, 181; 726/2, 21, 36; 380/255, 264, 276
See application file for complete search history.

(56) References Cited

U.S. PATENT DOCUMENTS

2007/0094501 A1* 4/2007 Takamizawa ....... H04L 63/0861
713/170
2010/0253471 A1 10/2010 Abe
(Continued)

FOREIGN PATENT DOCUMENTS

CN 101957898 A 1/2011
CN 105078427 A 11/2015
(Continued)

OTHER PUBLICATIONS

European Search Report dated May 2, 2018.
Chinese Search Report dated Jul. 28, 2021.

*Primary Examiner* — Sharif E Ullah
(74) *Attorney, Agent, or Firm* — Cha & Reiter, LLC

(57) ABSTRACT

An electronic device and method are disclosed. The electronic device includes a communication circuit, a memory storing identifiers for one or more external electronic devices defined as a group, and a processor. The processor implements the method, including receiving biometric information detected by an external biometric detection device via transmission from at least one external electronic device of the group, selecting from within the group a particular external electronic device based on the received biometric information and the information related to the particular external electronic device, and transmitting the received biometric information to the selected particular external electronic device.

6 Claims, 19 Drawing Sheets

(51) Int. Cl.
  *A61B 5/00* (2006.01)
  *G16H 15/00* (2018.01)
  *G16H 50/70* (2018.01)

(56) References Cited

U.S. PATENT DOCUMENTS

| | | |
|---|---|---|
| 2011/0012711 A1 | 1/2011 | Abe |
| 2014/0136720 A1* | 5/2014 | Bonazzoli ............ H04W 12/069 |
| | | 709/229 |
| 2015/0333870 A1* | 11/2015 | Chaturvedi ............ H04L 67/306 |
| | | 714/749 |
| 2016/0220170 A1 | 8/2016 | Hasegawa et al. |
| 2016/0249857 A1* | 9/2016 | Choi ....................... A61B 5/067 |
| | | 600/547 |
| 2016/0249864 A1 | 9/2016 | Kang et al. |
| 2017/0147360 A1* | 5/2017 | Reunamaki ......... H04L 41/0806 |

FOREIGN PATENT DOCUMENTS

| | | |
|---|---|---|
| CN | 105930631 A | 9/2016 |
| EP | 2261831 A2 | 12/2010 |
| KR | 10-0899041 B1 | 5/2009 |
| KR | 10-2013-0006968 A | 1/2013 |
| WO | 2016/148363 A1 | 9/2016 |
| WO | 2017/105085 A1 | 6/2017 |

* cited by examiner

ELECTRONIC DEVICE AND METHOD FOR MANAGING BODY INFORMATION BY ELECTRONIC DEVICE

CLAIM OF PRIORITY

This application claims the benefit under 35 U.S.C. § 119(a) of a Korean patent application filed in the Korean Intellectual Property Office on Dec. 19, 2016 and assigned Serial No. 10-2016-0173846, the entire disclosure of which is incorporated herein by reference.

TECHNICAL FIELD

The present disclosure relates to electronic devices, and more particularly, to detecting, providing, sharing and managing biometric body information.

BACKGROUND

Increasing interest in health and wellness drives systematic approaches for weight loss and health care by obtaining body fat or other body information in daily life. Therefore, body information obtaining devices can present weight measurements and checks on various health conditions in a systematical way. Recently gaining popularity are healthcare devices that can analyze various biological signals, including muscle mass, body water, body fat percentage, or others, by measuring the amount of body fat, leaving the user in a healthful condition.

The widespread use of multi-functional portable electronic devices, e.g., smartphones or tablet PCs, is also leading to increasing demand for checkup and management of the user's body conditions anytime, anywhere, through his/her portable electronic device.

A body information obtaining device may come with a communication module. The body information obtaining device may provide body information detected from the user through the communication module to the user's electronic device.

Serial communication, Bluetooth, Bluetooth Smart, or Wi-Fi technology is typically adopted for data transmission from such body information obtaining devices. Serial communication and Bluetooth or Bluetooth Smart enables the body information obtaining device to send data to a user device that it has established a communication link or paired with. Wi-Fi enables peer-to-multiple data communication among several user terminals that are linked to the body information obtaining device.

Conventional serial communication-capable body information obtaining devices may be able to send data to a single electronic device, requiring the user to plug her electronic device to the connection port of the body information obtaining device before transmitting body information detected or obtained. Bluetooth or Bluetooth Smart-capable body information obtaining devices need to be paired with a single electronic device before starting data transmission. Further, forgetting pairing with her electronic device, the body information obtaining device may end up pairing with a wrong electronic device, causing personal information leakage. Wi-Fi-capable body information obtaining devices, despite the advantages of the one-to-multiple data transmission, still suffer from a failure to differentiate the user's information from others' or exposure of her personal information to others.

The above information is presented as background information to assist with an understanding of the present disclosure. No determination has been made, and no assertion is made, as to whether any of the above might be applicable as prior art with regard to the present disclosure.

SUMMARY

According to an embodiment of the present disclosure, there may be provided an electronic device and method for managing body information by the same, which may provide body information obtained by a communication-capable body information obtaining device to an electronic device corresponding to the detected body information among a plurality of electronic devices when a plurality of users use the body information obtaining device regardless of how many users make use of the body information obtaining device.

According to an embodiment of the present disclosure, an electronic device is disclosed, including a communication circuit, a memory storing identifiers for one or more external electronic devices defined as a group, and a processor configured to: receive biometric information detected by an external biometric detection device via transmission from at least one external electronic device of the group, select from within the group a particular external electronic device based on the received biometric information and the information related to the particular external electronic device, and transmit the received biometric information to the selected particular external electronic device.

According to an embodiment of the present disclosure, a non-transitory storage medium storing commands executable by at least one processor of an electronic device to cause the processor to: store in a memory identifiers for one or more external electronic devices defined as a group, receive biometric information detected by an external biometric detection device via transmission from at least one external electronic device of the group, select from within the group a particular external electronic device based on the received biometric information and the information related to the particular external electronic device, and transmit the received biometric information to the selected particular external electronic device.

According to an embodiment of the present disclosure, an electronic device is disclosed, including a communication circuit for communicatively coupling with an external electronic device, a memory storing biometric information received from an external biometric detection device, and a processor configured to transmit the stored biometric information to a server, receive from the server biometric information, and an instruction corresponding to the received biometric information, and process the received s biometric information based on the received instruction. Other aspects and salient features of the disclosure will become apparent to those skilled in the art from the following detailed description, which, taken in conjunction with the annexed drawings, discloses example embodiments of the disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, such that.

Throughout the drawings, like reference numerals will be understood to refer to like parts, components, and structures.

DETAILED DESCRIPTION

Figure 1:
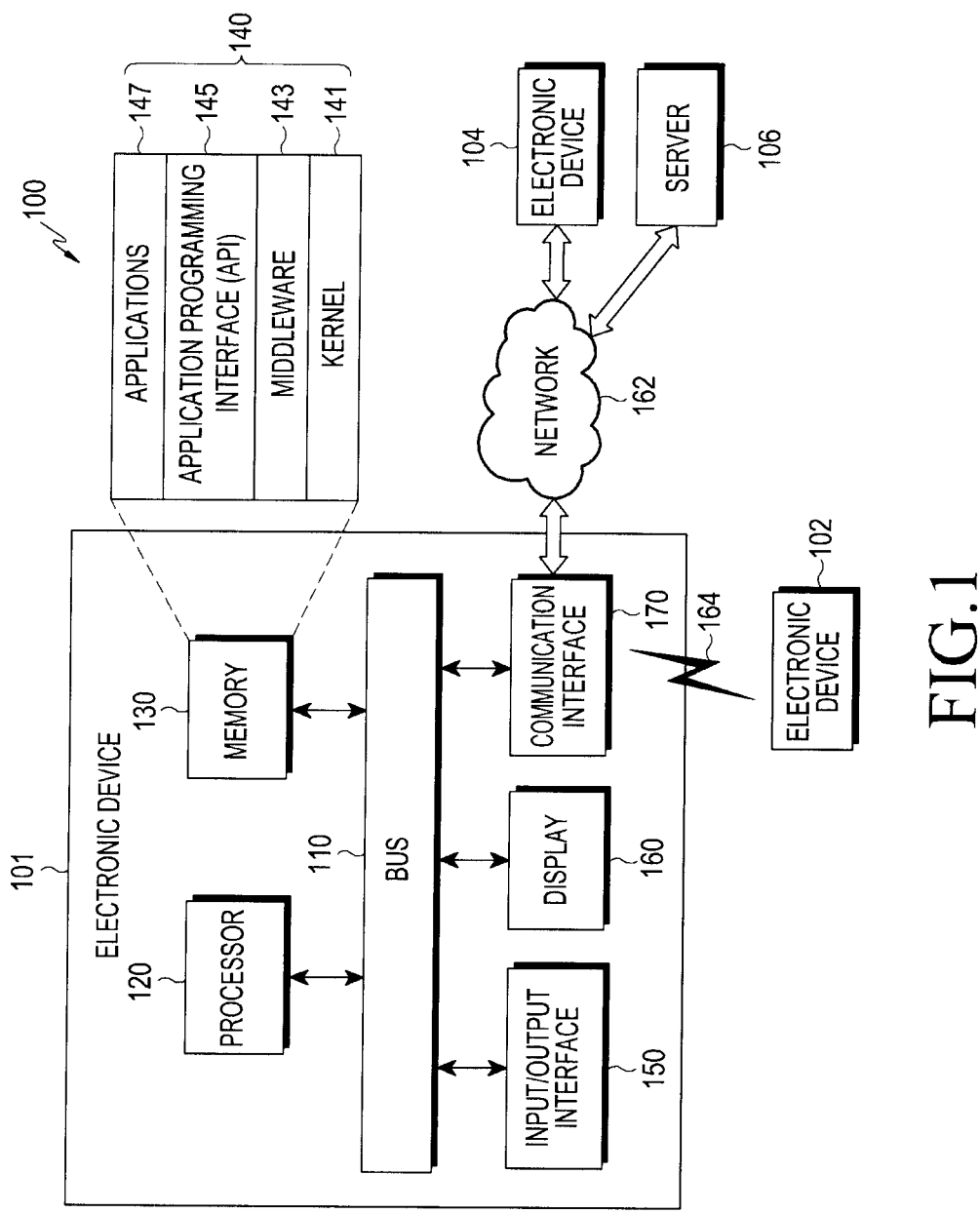
FIG. 1 is a view illustrating an electronic device in a network environment according to an embodiment of the present disclosure.

Hereinafter, embodiments of the present disclosure are described with reference to the accompanying drawings. However, it should be appreciated that the present disclosure is not limited to the embodiments and the terminology used herein, and all changes and/or equivalents or replacements thereto also belong to the present disclosure. The same or similar reference denotations may be used to refer to the same or similar elements throughout the specification and the drawings. It is to be understood that the singular forms "a," "an," and "the" include plural references unless the context clearly dictates otherwise. As used herein, the terms "A or B" or "at least one of A and/or B" may include all possible combinations of A and B. As used herein, the terms "first" and "second" may modify various components regardless of importance and/or order and are used to distinguish a component from another without limiting the components. It will be understood that when an element (e.g., a first element) is referred to as being (operatively or communicatively) "coupled with/to," or "connected with/to" another element (e.g., a second element), it can be coupled or connected with/to the other element directly or via a third element.

As used herein, the terms "configured to" may be interchangeably used with other terms, such as "suitable for," "capable of," "modified to," "made to," "adapted to," "able to," or "designed to" in hardware or software in the context. Rather, the term "configured to" may mean that a device can perform an operation together with another device or parts. For example, the term "processor configured (or set) to perform A, B, and C" may mean a generic-purpose processor (e.g., a CPU or application processor) that may perform the operations by executing one or more software programs stored in a memory device or a dedicated processor (e.g., an embedded processor) for performing the operations.

For example, examples of the electronic device according to embodiments of the present disclosure may include at least one of a smartphone, a tablet personal computer (PC), a mobile phone, a video phone, an e-book reader, a desktop PC, a laptop computer, a netbook computer, a workstation, a server, a personal digital assistant (PDA), a portable multimedia player (PMP), a MP3 player, a medical device, a camera, or a wearable device. The wearable device may include at least one of an accessory-type device (e.g., a watch, a ring, a bracelet, an anklet, a necklace, glasses, contact lenses, or a head-mounted device (HMD)), a fabric- or clothes-integrated device (e.g., electronic clothes), a body attaching-type device (e.g., a skin pad or tattoo), or a body implantable device. In some embodiments, examples of the smart home appliance may include at least one of a television, a digital video disk (DVD) player, an audio player, a refrigerator, an air conditioner, a cleaner, an oven, a microwave oven, a washer, a drier, an air cleaner, a set-top box, a home automation control panel, a security control panel, a TV box (e.g., Samsung HomeSync™, Apple TV™, or Google TV™), a gaming console (Xbox™, PlayStation™), an electronic dictionary, an electronic key, a camcorder, or an electronic picture frame.

According to an embodiment of the present disclosure, the electronic device may include at least one of various medical devices (e.g., diverse portable medical measuring devices (a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global navigation satellite system (GNSS) receiver, an event data recorder (EDR), a flight data recorder (FDR), an automotive infotainment device, an sailing electronic device (e.g., a sailing navigation device or a gyro compass), avionics, security devices, vehicular head units, industrial or home robots, drones, automatic teller's machines (ATMs), point of sales (POS) devices, or internet of things (IoT) devices (e.g., a bulb, various sensors, a sprinkler, a fire alarm, a thermostat, a street light, a toaster, fitness equipment, a hot water tank, a heater, or a boiler). According to various embodiments of the disclosure, examples of the electronic device may at least one of part of a piece of furniture, building/structure or vehicle, an electronic board, an electronic signature receiving device, a projector, or various measurement devices (e.g., devices for measuring water, electricity, gas, or electromagnetic waves). According to embodiments of the present disclosure, the electronic device may be flexible or may be a combination of the above-enumerated electronic devices. According to an embodiment of the present disclosure, the electronic device is not limited to the above-listed embodiments. As used herein, the term "user" may denote a human or another device (e.g., an artificial intelligent electronic device) using the electronic device.

Referring to FIG. 1, according to an embodiment of the present disclosure, an electronic device 101 is included in a network environment 100. The electronic device 101 may include a bus 110, a processor 120, a memory 130, an input/output interface 150, a display 160, and a communication interface 170. In some embodiments, the electronic device 101 may exclude at least one of the components or may add another component. The bus 110 may include a circuit for connecting the components 110 to 170 with one another and transferring communications (e.g., control messages or data) between the components. The processor 120 may include one or more of a central processing unit (CPU), an application processor (AP), or a communication processor (CP). The processor 120 may perform control on at least one of the other components of the electronic device 101, and/or perform an operation or data processing relating to communication.

The memory 130 may include a volatile and/or non-volatile memory. For example, the memory 130 may store commands or data related to at least one other component of the electronic device 101. According to an embodiment of the present disclosure, the memory 130 may store software and/or a program 140. The program 140 may include, e.g., a kernel 141, middleware 143, an application programming interface (API) 145, and/or an application program (or "application") 147. At least a portion of the kernel 141, middleware 143, or API 145 may be denoted an operating system (OS). For example, the kernel 141 may control or manage system resources (e.g., the bus 110, processor 120, or a memory 130) used to perform operations or functions implemented in other programs (e.g., the middleware 143, API 145, or application program 147). The kernel 141 may provide an interface that allows the middleware 143, the API 145, or the application 147 to access the individual components of the electronic device 101 to control or manage the system resources.

The middleware 143 may function as a relay to allow the API 145 or the application 147 to communicate data with the kernel 141, for example. Further, the middleware 143 may process one or more task requests received from the application program 147 in order of priority. For example, the middleware 143 may assign a priority of using system resources (e.g., bus 110, processor 120, or memory 130) of the electronic device 101 to at least one of the application programs 147 and process one or more task requests. The API 145 is an interface allowing the application 147 to control functions provided from the kernel 141 or the middleware 143. For example, the API 133 may include at least one interface or function (e.g., a command) for filing control, window control, image processing or text control. For example, the input/output interface 150 may transfer commands or data input from the user or other external device to other component(s) of the electronic device 101 or may output commands or data received from other component(s) of the electronic device 101 to the user or other external devices.

The display 160 may include, e.g., a liquid crystal display (LCD), a light emitting diode (LED) display, an organic light emitting diode (OLED) display, or a microelectromechanical systems (MEMS) display, or an electronic paper display. The display 160 may display, e.g., various contents (e.g., text, images, videos, icons, or symbols) to the user. The display 160 may include a touchscreen and may receive, e.g., a touch, gesture, proximity or hovering input using an electronic pen or a body portion of the user. For example, the communication interface 170 may set up communication between the electronic device 101 and an external electronic device (e.g., a first electronic device 102, a second electronic device 104, or a server 106). For example, the communication interface 170 may be connected with a network 162 through wireless communication or wired communication and may communicate with an external device (e.g., the second external electronic device 104 or server 106) or through short range network communication 164.

The wireless communication may include cellular communication which uses at least one of, e.g., long term evolution (LTE), long term evolution-advanced (LTE-A), code division multiple access (CDMA), wideband code division multiple access (WCDMA), universal mobile telecommunication system (UMTS), wireless broadband (Wi-Bro), or global system for mobile communication (GSM). According to an embodiment of the present disclosure, the wireless communication may include at least one of, e.g., wireless fidelity (Wi-Fi), BlueTooth, BlueTooth low power (BLE), zigbee, near field communication (NFC), magnetic secure transmission (MST), radio frequency, or body area network (BAN). According to an embodiment of the present disclosure, the wireless communication may include global navigation satellite system (GNSS). The GNSS may be, e.g., global positioning system (GPS), global navigation satellite system (Glonass), Beidou navigation satellite system (hereinafter, "Beidou") or Galileo, or the European global satellite-based navigation system. Hereinafter, the terms "GPS" and the "GNSS" may be interchangeably used herein. The wired connection may include at least one of, e.g., universal serial bus (USB), high definition multimedia interface (HDMI), recommended standard (RS)-232, power line communication (PLC), or plain old telephone service (POTS). The network 162 may include at least one of telecommunication networks, e.g., a computer network (e.g., local area network (LAN) or wide area network (WAN)), Internet, or a telephone network.

The first and second external electronic devices 102 and 104 each may be a device of the same or a different type from the electronic device 101. According to an embodiment of the present disclosure, all or some of operations executed on the electronic device 101 may be executed on another or multiple other electronic devices (e.g., the electronic devices 102 and 104 or server 106). According to an embodiment of the present disclosure, when the electronic device 101 should perform some function or service automatically or at a request, the electronic device 101, instead of executing the function or service on its own or additionally, may request another device (e.g., electronic devices 102 and 104 or server 106) to perform at least some functions associated therewith. The other electronic device (e.g., electronic devices 102 and 104 or server 106) may execute the requested functions or additional functions and transfer a result of the execution to the electronic device 101. The electronic device 101 may provide a requested function or service by processing the received result as it is or additionally. To that end, a cloud computing, distributed computing, or client-server computing technique may be used, for example.

Figure 2:
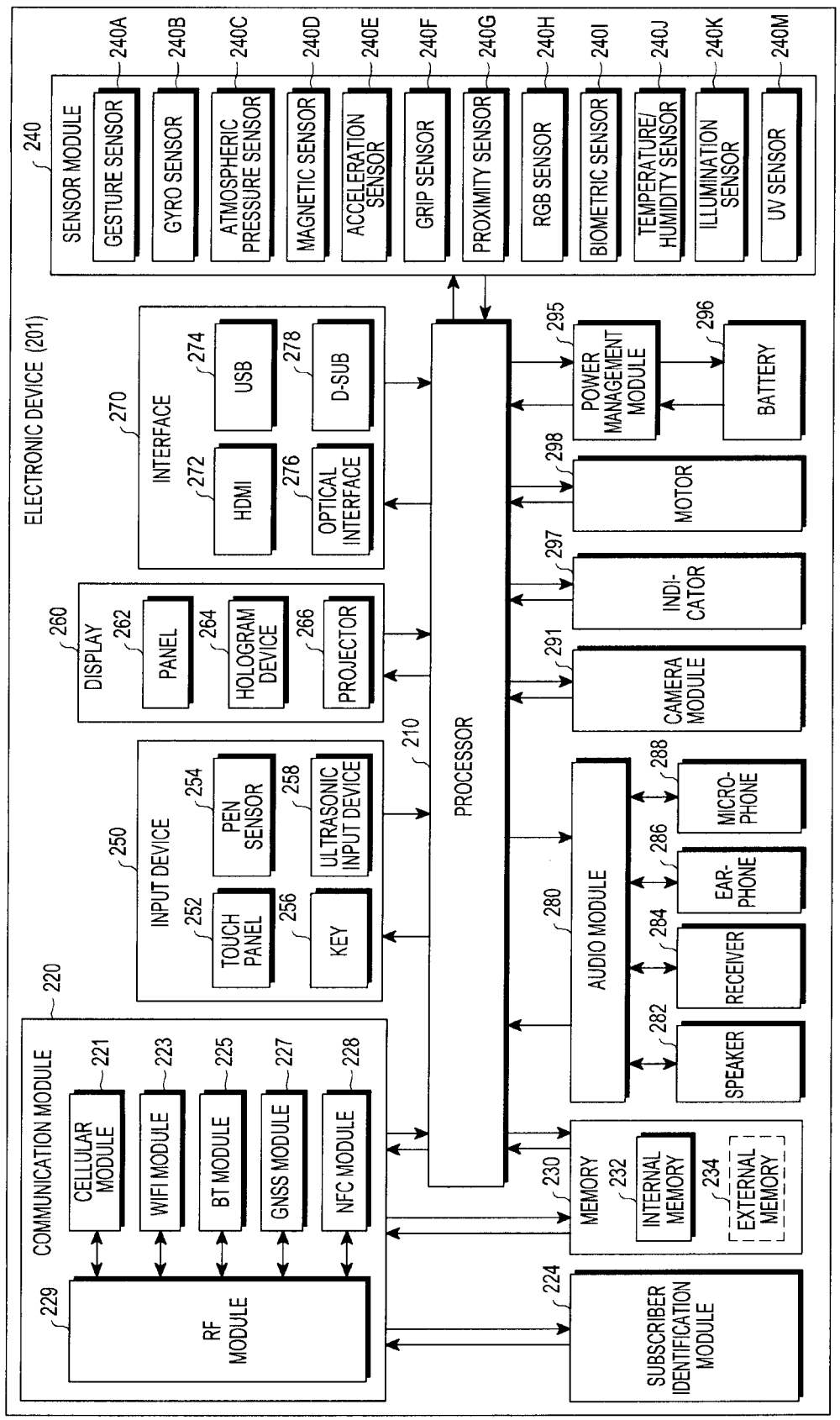
FIG. 2 is a block diagram illustrating an electronic device according to an embodiment of the present disclosure.

FIG. 2 is a block diagram illustrating an electronic device 201 according to an embodiment of the present disclosure. The electronic device 201 may include the whole or part of, e.g., the electronic device 101 shown in FIG. 1. The electronic device 201 may include one or more processors (e.g., application processors (APs)) 210, a communication module 220, a subscriber identification module (SIM) 224, a memory 230, a sensor module 240, an input unit 250, a display 260, an interface 270, an audio module 280, a camera module 291, a power management module 295, a battery 296, an indicator 297, and a motor 298. The processor 210 may control multiple hardware and software components connected to the processor 210 by running, e.g., an operating system or application programs, and the processor 210 may process and compute various data. The processor 210 may be implemented in, e.g., a system on chip (SoC). According to an embodiment of the present disclosure, the processor 210 may further include a graphic processing unit (GPU) and/or an image signal processor. The processor 210 may include at least some (e.g., the cellular module 221) of the components shown in FIG. 2. The processor 210 may load a command or data received from at least one of other components (e.g., a non-volatile memory) on a volatile memory, process the command or data, and store resultant data in the non-volatile memory.

The communication module 220 may have the same or similar configuration to the communication interface 170. The communication module 220 may include, e.g., a cellular module 221, a wireless fidelity (Wi-Fi) module 223, a BlueTooth (BT) module 225, a GNSS module 227, a NFC module 228, and a RF module 229. The cellular module 221 may provide voice call, video call, text, or Internet services through, e.g., a communication network. The cellular module 221 may perform identification or authentication on the electronic device 201 in the communication network using a subscriber identification module 224 (e.g., the SIM card). According to an embodiment of the present disclosure, the cellular module 221 may perform at least some of the functions providable by the processor 210. According to an embodiment of the present disclosure, the cellular module 221 may include a communication processor (CP). According to an embodiment of the present disclosure, at least some (e.g., two or more) of the cellular module 221, the Wi-Fi module 223, the Bluetooth module 225, the GNSS module 227, or the NFC module 228 may be included in a single integrated circuit (IC) or an IC package. The RF module 229 may communicate data, e.g., communication signals (e.g., RF signals). The RF module 229 may include, e.g., a transceiver, a power amp module (PAM), a frequency filter, a low noise amplifier (LNA), or an antenna. According to an embodiment of the present disclosure, at least one of the cellular module 221, the Wi-Fi module 223, the BlueTooth module 225, the GNSS module 227, or the NFC module 228 may communicate RF signals through a separate RF module. The subscriber identification module 224 may include, e.g., a card including a subscriber identification module, or an embedded SIM, and may contain unique identification information (e.g., an integrated circuit card identifier (IC-CID) or subscriber information (e.g., an international mobile subscriber identity (IMSI)).

The memory 230 (e.g., the memory 130) may include, e.g., an internal memory 232 or an external memory 234. The internal memory 232 may include at least one of, e.g., a volatile memory (e.g., a dynamic RAM (DRAM), a static RAM (SRAM), a synchronous dynamic RAM (SDRAM), etc.) or a non-volatile memory (e.g., a one-time programmable ROM (OTPROM), a programmable ROM (PROM), an erasable and programmable ROM (EPROM), an electrically erasable and programmable ROM (EEPROM), a mask ROM, a flash ROM, a flash memory (e.g., a NAND flash, or a NOR flash), a hard drive, or solid state drive (SSD). The external memory 234 may include a flash drive, e.g., a compact flash (CF) memory, a secure digital (SD) memory, a micro-SD memory, a min-SD memory, an extreme digital (xD) memory, a multi-media card (MMC), or a memory stick™. The external memory 234 may be functionally or physically connected with the electronic device 201 via various interfaces.

For example, the sensor module 240 may measure a physical quantity or detect an motion state of the electronic device 201, and the sensor module 240 may convert the measured or detected information into an electrical signal. The sensor module 240 may include at least one of, e.g., a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (e.g., a red-green-blue (RGB) sensor, a bio sensor 240I, a temperature/humidity sensor 240J, an illumination sensor 240K, or an Ultra Violet (UV) sensor 240M. Additionally or alternatively, the sensor module 240 may include, e.g., an e-nose sensor, an electromyography (EMG) sensor, an electroencephalogram (EEG) sensor, an electrocardiogram (ECG) sensor, an infrared (IR) sensor, an iris sensor, or a finger print sensor. The sensor module 240 may further include a control circuit for controlling at least one or more of the sensors included in the sensing module. According to an embodiment of the present disclosure, the electronic device 201 may further include a processor configured to control the sensor module 240 as part of the processor 210 or separately from the processor 210, and the electronic device 2701 may control the sensor module 240 while the processor 210 is in a sleep mode.

The input unit 250 may include, e.g., a touch panel 252, a (digital) pen sensor 254, a key 256, or an ultrasonic input device 258. The touch panel 252 may use at least one of capacitive, resistive, infrared, or ultrasonic methods. The touch panel 252 may further include a control circuit. The touch panel 252 may further include a tactile layer and may provide a user with a tactile reaction. The (digital) pen sensor 254 may include, e.g., a part of a touch panel or a separate sheet for recognition. The key 256 may include e.g., a physical button, optical key or key pad. The ultrasonic input device 258 may sense an ultrasonic wave generated from an input tool through a microphone (e.g., the microphone 288) to identify data corresponding to the sensed ultrasonic wave.

The display 260 (e.g., the display 160) may include a panel 262, a hologram device 264, a projector 266, and/or a control circuit for controlling the same. The panel 262 may be implemented to be flexible, transparent, or wearable. The panel 262, together with the touch panel 252, may be configured in one or more modules. According to an embodiment of the present disclosure, the panel 262 may include a pressure sensor (or pose sensor) that may measure the strength of a pressure by the user's touch. The pressure sensor may be implemented in a single body with the touch panel 252 or may be implemented in one or more sensors separate from the touch panel 252. The hologram device 264 may make three dimensional (3D) images (holograms) in the air by using light interference. The projector 266 may display an image by projecting light onto a screen. The screen may be, for example, located inside or outside of the electronic device 201. The interface 270 may include e.g., a high definition multimedia interface (HDMI) 272, a USB 274, an optical interface 276, or a D-subminiature (D-sub) 278. The interface 270 may be included in e.g., the communication interface 170 shown in FIG. 1. Additionally or alternatively, the interface 270 may include a mobile high-definition link (MHL) interface, a secure digital (SD) card/ multimedia card (MMC) interface, or infrared data association (IrDA) standard interface.

The audio module 280 may converting, e.g., a sound signal into an electrical signal and vice versa. At least a part of the audio module 280 may be included in e.g., the input/output interface 145 as shown in FIG. 1. The audio module 280 may process sound information input or output through e.g., a speaker 282, a receiver 284, an earphone 286, or a microphone 288. For example, the camera module 291 may be a device for capturing still images and videos, and may include, according to an embodiment of the present disclosure, one or more image sensors (e.g., front and back sensors), a lens, an image signal processor (ISP), or a flash such as an LED or xenon lamp. The power manager module 295 may manage power of the electronic device 201, for example. According to an embodiment of the present disclosure, the power manager module 295 may include a power management Integrated circuit (PMIC), a charger IC, or a battery or fuel gauge. The PMIC may have a wired and/or wireless recharging scheme. The wireless charging scheme may include e.g., a magnetic resonance scheme, a magnetic induction scheme, or an electromagnetic wave based scheme, and an additional circuit, such as a coil loop, a resonance circuit, a rectifier, or the like may be added for wireless charging. The battery gauge may measure an amount of remaining power of the battery 296, a voltage, a current, or a temperature while the battery 296 is being charged. The battery 296 may include, e.g., a rechargeable battery or a solar battery.

The indicator 297 may indicate a particular state of the electronic device 201 or a part (e.g., the processor 210) of the electronic device, including e.g., a booting state, a message state, or recharging state. The motor 298 may convert an electric signal to a mechanical vibration and may generate a vibrational or haptic effect. The electronic device 201 may include a mobile TV supporting device (e.g., a GPU) that may process media data as per, e.g., digital multimedia broadcasting (DMB), digital video broadcasting (DVB), or mediaFlo™ standards. Each of the aforementioned components of the electronic device may include one or more parts, and a name of the part may vary with a type of the electronic device. According to various embodiments, the electronic device (e.g., the electronic device 201) may exclude some elements or include more elements, or some of the elements may be combined into a single entity that may perform the same function as by the elements before combined.

Figure 3:
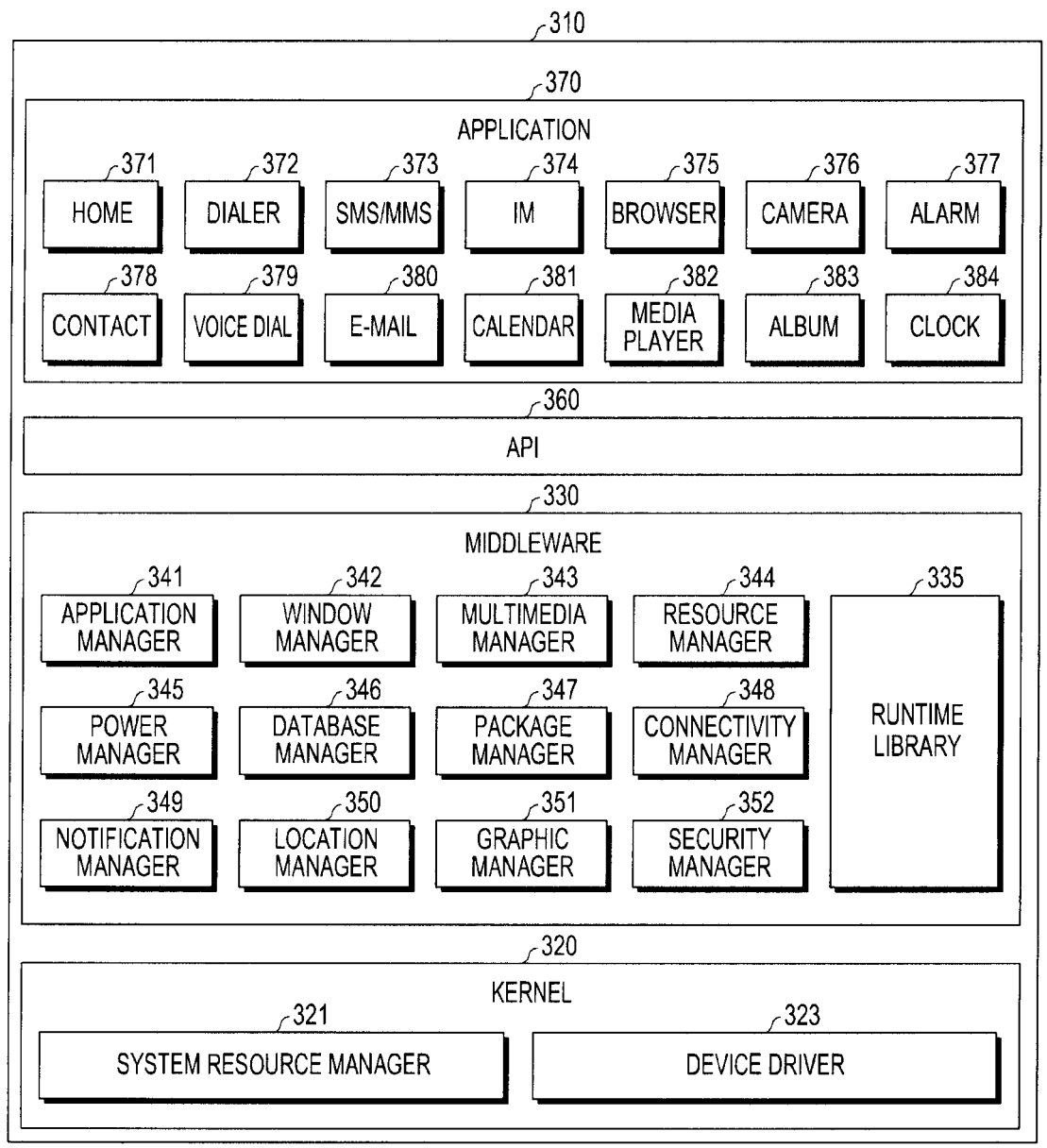
FIG. 3 is a block diagram illustrating a program module according to an embodiment of the present disclosure.

FIG. 3 is a block diagram illustrating a program module according to an embodiment of the present disclosure. According to an embodiment of the present disclosure, the program module 310 (e.g., the program 140) may include an operating system (OS) controlling resources related to the electronic device (e.g., the electronic device 101) and/or various applications (e.g., the application processor 210) driven on the operating system. The OS may include, e.g., Android™, iOS™, Windows™, Symbian™, Tizen™, or Bada™. Referring to FIG. 3, the program module 310 may include a kernel 320 (e.g., the kernel 141), middleware 330 (e.g., the middleware 143), an API 360 (e.g., the API 145), and/or an application 370 (e.g., the application program 147). At least a part of the program module 310 may be preloaded on the electronic device or may be downloaded from an external electronic device (e.g., the electronic devices 102 and 104 or server 106).

The kernel 320 may include, e.g., a system resource manager 321 or a device driver 323. The system resource manager 321 may perform control, allocation, or recovery of system resources. According to an embodiment of the present disclosure, the system resource manager 321 may include a process managing unit, a memory managing unit, or a file system managing unit. The device driver 323 may include, e.g., a display driver, a camera driver, a BlueTooth driver, a shared memory driver, a USB driver, a keypad driver, a Wi-Fi driver, an audio driver, or an inter-process communication (IPC) driver. The middleware 330 may provide various functions to the application 370 through the API 360 so that the application 370 may use limited system resources in the electronic device or provide functions jointly utilized by applications 370. According to an embodiment of the present disclosure, the middleware 330 may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, or a security manager 352.

The runtime library 335 may include a library module used by a compiler in order to add a new function through a programming language while, e.g., the application 370 is being executed. The runtime library 335 may perform input/output management, memory management, or arithmetic function processing. The application manager 341 may manage the life cycle of, e.g., the applications 370. The window manager 342 may manage GUI resources used on the screen. The multimedia manager 343 may grasp formats utilized to play media files and use a codec appropriate for a format to perform encoding or decoding on media files. The resource manager 344 may manage the source code or memory space of the application 370. The power manager 345 may manage, e.g., the battery capability or power and provide power information utilized for the operation of the electronic device. According to an embodiment of the present disclosure, the power manager 345 may interwork with a basic input/output system (BIOS). The database manager 346 may generate, search, or vary a database to be used in the applications 370. The package manager 347 may manage installation or update of an application that is distributed in the form of a package file.

The connectivity manager 348 may manage, e.g., wireless connectivity. The notification manager 349 may provide an event, e.g., arrival message, appointment, or proximity alert, to the user. The location manager 350 may manage, e.g., locational information on the electronic device. The graphic manager 351 may manage, e.g., graphic effects to be offered to the user and their related user interface. The security manager 352 may provide system security or user authentication, for example. According to an embodiment of the present disclosure, the middleware 330 may include a telephony manager for managing the voice or video call function of the electronic device or a middleware module able to form a combination of the functions of the above-described elements. According to an embodiment of the present disclosure, the middleware 330 may provide a module specified according to the type of the operating system. The middleware 330 may dynamically omit some existing components or add new components. The API 360 may be a set of, e.g., API programming functions and may have different configurations depending on operating systems. For example, in the case of Android or iOS, one API set may be provided per platform, and in the case of Tizen, two or more API sets may be offered per platform.

The application 370 may include an application that may provide, e.g., a home 371, a dialer 372, an SMS/MMS 373, an instant message (IM) 374, a browser 375, a camera 376, an alarm 377, a contact 378, a voice dial 379, an email 380, a calendar 381, a media player 382, an album 383, or a clock 384, a health-care (e.g., measuring the degree of workout or blood sugar), or provision of environmental information (e.g., provision of air pressure, moisture, or temperature information). According to an embodiment of the present disclosure, the application 370 may include an information exchanging application supporting information exchange between the electronic device and an external electronic device. Examples of the information exchange application may include, but is not limited to, a notification relay application for transferring specific information to the external electronic device, or a device management application for managing the external electronic device. For example, the notification relay application may transfer notification information generated by other application of the electronic device to the external electronic device or receive notification information from the external electronic device and provide the received notification information to the user. For example, the device management application may install, delete, or update a function (e.g., turn-on/turn-off the external electronic device (or some elements) or adjusting the brightness (or resolution) of the display) of the external electronic device communicating with the electronic device or an application operating on the external electronic device. According to an embodiment of the present disclosure, the application 370 may include an application (e.g., a healthcare application of a mobile medical device) designated according to an attribute of the external electronic device. According to an embodiment of the present disclosure, the application 370 may include an application received from the external electronic device. At least a portion of the program module 310 may be implemented (e.g., executed) in software, firmware, hardware (e.g., the processor 210), or a combination of at least two or more thereof and may include a module, program, routine, command set, or process for performing one or more functions.

FIGS. 4A to 4D are views schematically illustrating a body information managing method in a body information managing system according to an embodiment of the present disclosure. FIGS. 4A to 4D illustrate components related to embodiments of the present disclosure, and other components than the above-listed components may also be included. In FIGS. 4A to 4D, a first electronic device 401-1 of a plurality of electronic devices 401-1 to 401-n may be communicatively coupled to a body information obtaining device 400, and an electronic device corresponding to body information 400a obtained by the body information obtaining device 400 may correspond to a second electronic device 401-2.

Figure 4A:
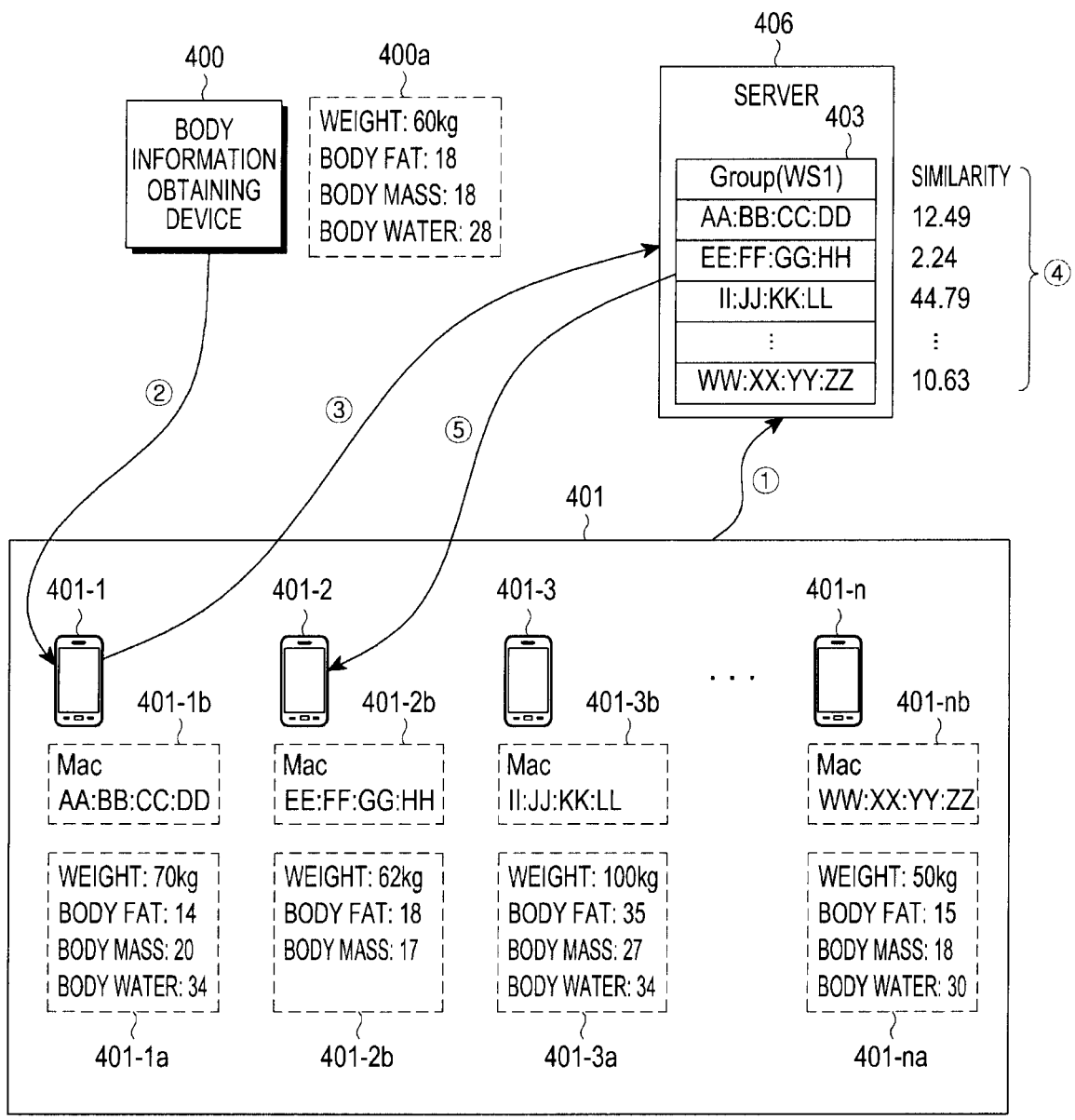
FIG. 4A, FIG. 4B, FIG. 4C and FIG. 4D are views schematically illustrating a body information managing method in a body information managing system according to an embodiment of the present disclosure.

Referring to FIG. 4A, according to an embodiment of the present disclosure, a body information managing system may include a body information obtaining device 400, a plurality of electronic devices 401-1 to 401-n, and a server 406. The body information obtaining device 400 (e.g., a biometric detection device) may include communication functionality. The body information obtaining device 400 may include a communication circuit (not shown) capable of network communication with one of the plurality of electronic devices 401-1 to 401-n. The communication circuit (not shown) may include a short-range communication circuit capable of transmission of data (e.g., body information 400a) through short-range communication with one of the plurality of electronic devices 401-1 to 401-n. The body information obtaining device 400 may include at least one sensor (not shown) capable of detecting the user's body information (e.g., biometric information). The body information may include at least one of, e.g., the user's height, weight, body fat, bone mineral density, skeletal muscle mass, muscle strength, body water level, body fat (e.g., body mass index), basal metabolic rate, biological information, or a combination thereof. The biological information may include, e.g., a biological signal, such as, e.g., an electrocardiography (ECG) signal, an electroencephalogram (EEG) signal, an electrooculogram (EOG) signal, an electrogastrogram (EGG) signal, or an electromyography (EMG) signal, a heart rate, a cardiac cycle, a cardiac cycle standard deviation, a pulse rate, arrhythmia, blood volume impedance, or a stress level.

According to an embodiment of the present disclosure, the at least one sensor (not shown) may include at least one of a weight sensor capable of detecting the user's weight, a body composition sensor capable of measuring the body composition, a biological information sensor capable of detecting biological information, or a combination thereof. The at least one sensor, however, is not limited thereto, and any sensor may rather be included which is able to detect information related to the user's body.

The server 406 (e.g., an internet-of-things or "IoT" server) may communicate with the plurality of electronic devices 401-1 to 401-n associated with the body information obtaining device 400 through a network. For example, the server 406 may receive a request signal for registration in a group 403 (e.g., WS1) related to the body information obtaining device 400 from at least one electronic device 401-1 to 401-n associated with the body information obtaining device 400. The server 406, upon receiving the request signal, may generate a group 403 (e.g., WS1) related to the body information obtaining device 400 and then store and register (①) the corresponding electronic device in the group 403. The group 403 may store information related to the at least one electronic device 401-1 or information for a plurality of electronic devices 401 to 401-n. For example, the plurality of electronic devices 401-1 to 401-n may each send registration request messages for registration in the group 403 related to the body information obtaining device 400 to the server 406.

According to an embodiment of the present disclosure, the information related to a corresponding electronic device may include at least some of information (e.g., a device identification (ID)) for identifying the electronic device, group identification information (e.g., a group ID such as "WS1"), network address information (e.g., a media access control or "MAC" address), body information, information (e.g., a device ID) for identifying the body information obtaining device 400 associated with the electronic device, or a combination thereof. In response to the registration request signals, the server 406 may store the information related to each electronic device 401-1 to 401-n in the group 403.

The plurality of electronic devices 401-1 to 401-n may be portable electronic devices, such as smartphones or wearable devices with various functions including communication functionality. According to an embodiment of the present disclosure, the plurality of electronic devices 401-1 to 401-n may be at least one user's electronic device(s) sharing the body information obtaining device 400. Each electronic device 401-1 to 401-n may include the whole or part of the electronic device 101 of FIG. 1 or the electronic device 201 of FIG. 2. The user who uses the body information obtaining device 400 may detect or obtain body information 400a through the body information obtaining device 400, establish a communication link with the body information obtaining device 400, and receive the obtained body information 400a to her electronic device.

When the body information 400a of the user is obtained, the body information obtaining device 400 may transmit the obtained body information 400a to one of the electronic devices (e.g. 401-1 to 401-3) that is positioned within a communicable range (e.g., a short-range communication range) through the communication circuit (not shown) of the body information obtaining device 400, and is communicatively coupled to the device 400 among the plurality of electronic devices (e.g. 401-1 to 401-n) in the group 430. For example, where a first electronic device 401-1 among the plurality of electronic devices 401-1 to 401-n is the electronic device communicatively coupled to the body information obtaining device 4000 for communication, the body information obtaining device 400 may transmit (②) body information 400a obtained by the body information obtaining device 400 to the first electronic device 401-1. The body information 400a selected for transmission may be information is obtained by the user but has not yet been transmitted to any of the electronic devices 401-1 to 401-n included in the group 403.

The first electronic device 401-1, upon receipt of the body information 400a from the body information obtaining device 400, may transmit (③) the received body information 400a to the server 406.

Upon receiving the body information 400a, the server 406 may calculate (④) a similarity between the received body information 400a and the body information 401-1a to 401-na stored for each electronic device 401-1 to 401-n in the group 403. The server 406 may compare calculated similarities, and the server 406 may determine that the electronic device of the lowest similarity (e.g., a second electronic device 401-2) is the user's electronic device corresponding to the received body information 400a.

The server 406 may transmit (⑤) a signal containing the received body information 400a and a command for storing the received body information 400a to the second electronic device 401-2 based on network address information 401-2b of the information related to the second electronic device 401-2 determined to correspond to the received body information 400a.

The second electronic device 401-2 may cumulatively store the body information 400a received from the server 406 in a memory (e.g., the memory 130 or memory 230) of the second electronic device 401-2. The second electronic device 401-2 may update body information 401-2a previously stored in the memory (e.g., the memory 130 or memory 230) with the received body information 400a.

According to an embodiment of the present disclosure, upon receiving (②) the body information 400a from the body information obtaining device 400, the first electronic device 401-1 may determine the user's electronic device corresponding to the received body information 400a based on the similarity calculated by each electronic device 401-1 to 401-n, but not by the server 406. Its relevant embodiments are described below in greater detail with FIGS. 4B to 4D.

Figure 4B:
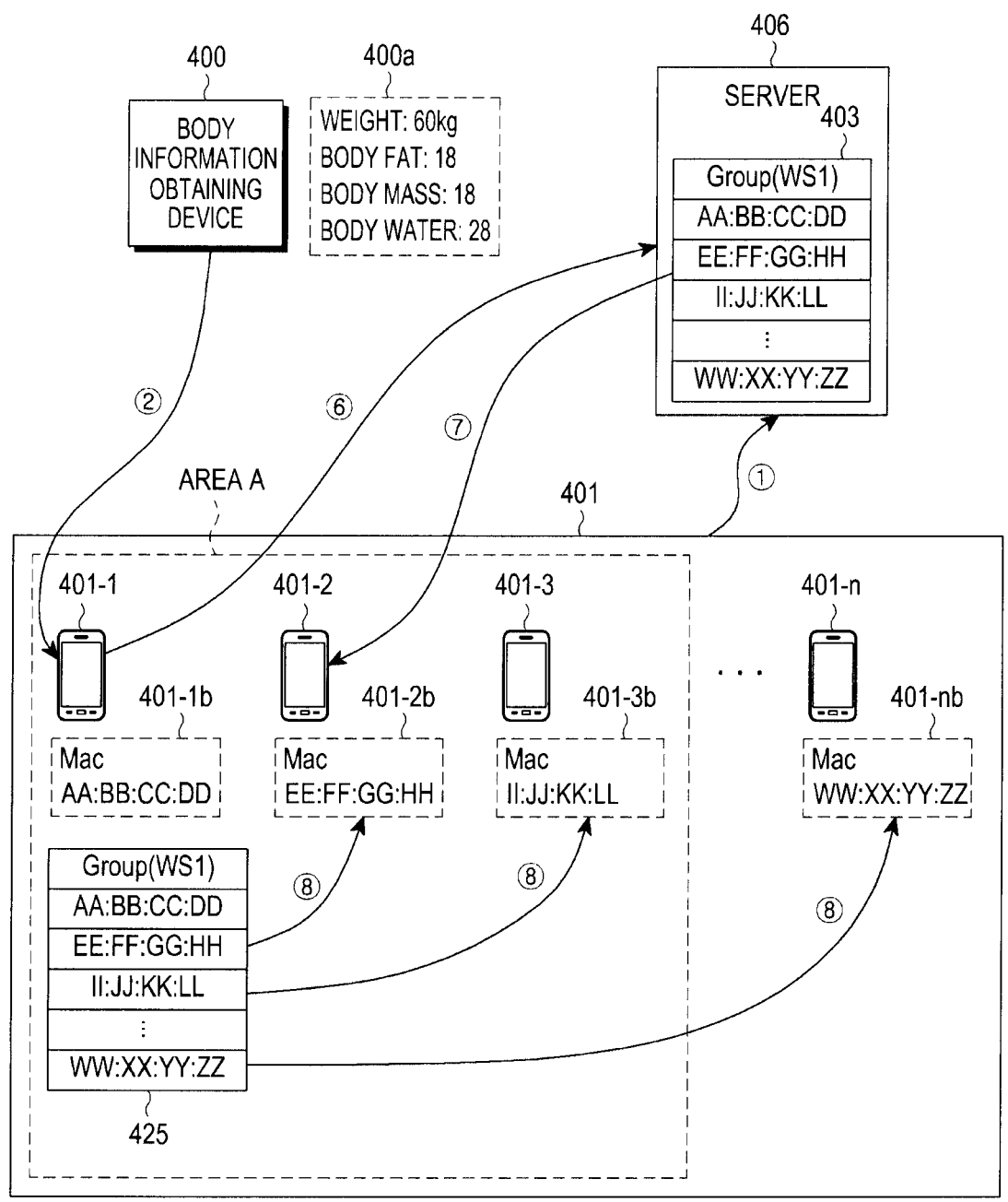

Referring to FIG. 4B, when the body information 400a is received from the body information obtaining device 400, the first electronic device 401-1 may transmit (⑥) a request for information (e.g., network address information such as a MAC address) related to the other electronic devices 401-2 to 401-n (included in the group 403) other than the first electronic device 401-1 related to the body information obtaining device 400 to the server 406. Operations ① and ② of FIG. 4B are the same as those of FIG. 4A, and no further detailed description is presented below.

In response to a receipt of the information request (⑥), the server 406 may transmit (⑦), to the first electronic device 401-1, the information (e.g., network address information) related to the other electronic devices 401-2 to 401-n in the group 403 than the first electronic device 401-1.

The first electronic device 401-1 may generate a group 425 (e.g., WS1) related to the body information obtaining device 400 based on the information (e.g., the network address information) related to the other electronic devices 401-2 to 401-n received from the server 406, and the first electronic device 401-1 may store the group 425 in the memory (not shown) of the first electronic device 401-1.

The first electronic device 401-1 may transmit (⑧) a signal containing the network address information 401-1b (e.g., MAC address (AA:BB:CC:DD)) of the first electronic device 401-1 and the body information 400a received from the body information obtaining device 400 to each of the electronic devices 401-2 to 401-n in the group 425 based on the network address information 401-2b to 401-nb of each electronic device 401-2 to 401-n in the group 425.

According to an embodiment of the present disclosure, upon transmission (⑧), an electronic device (e.g., a n-th electronic device 401-n) that is not within a communicable range (area A) of the first electronic device 401-1 among the electronic devices 401-2 to 401-n in the group 425 may fail to receive the body information 400a from the first electronic device 401-1.

Figure 4C:
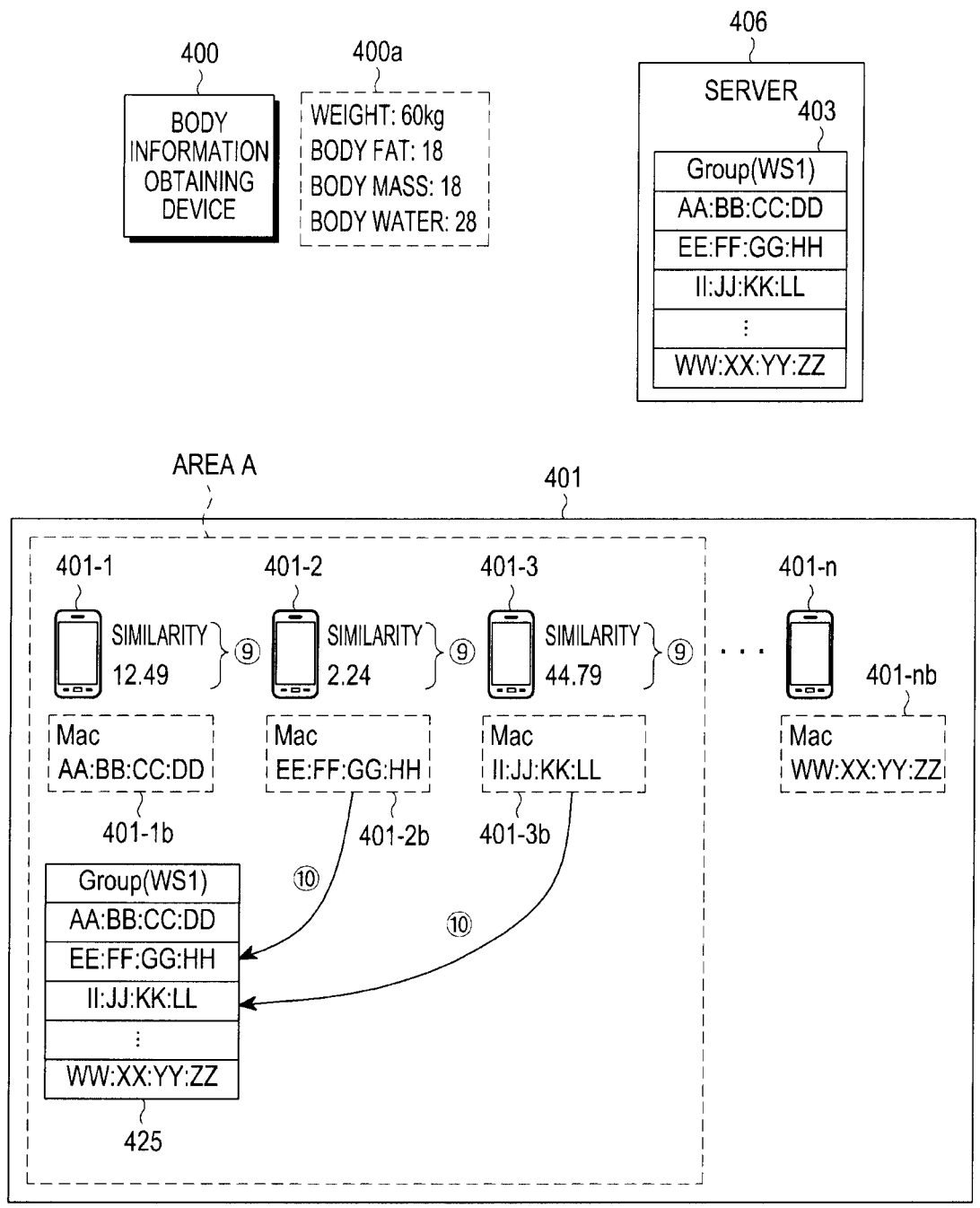

Referring to FIG. 4C, each of electronic devices (e.g., electronic devices 401-1 to 401-3) disposed within the communicable range (area A) (thus having received the body information 400a) may calculate (⑨) a similarity between the received body information 400a and its own body information previously stored therein. The previous body information previously stored in each electronic device 401-1 to 401-3 may be the latest body information that the corresponding electronic device has stored.

Each of electronic devices (e.g., electronic devices 401-1 to 401-3) disposed within the communicable range (area A) among the electronic devices 401-1 to 401-n in the group 425 and that has also received the body information 400a may transmit (⑩) the calculated similarity to the first electronic device 401-1 based on the network address information (e.g., "AA:BB:CC:DD") 401-1b of the first electronic device 401-1.

Figure 4D:
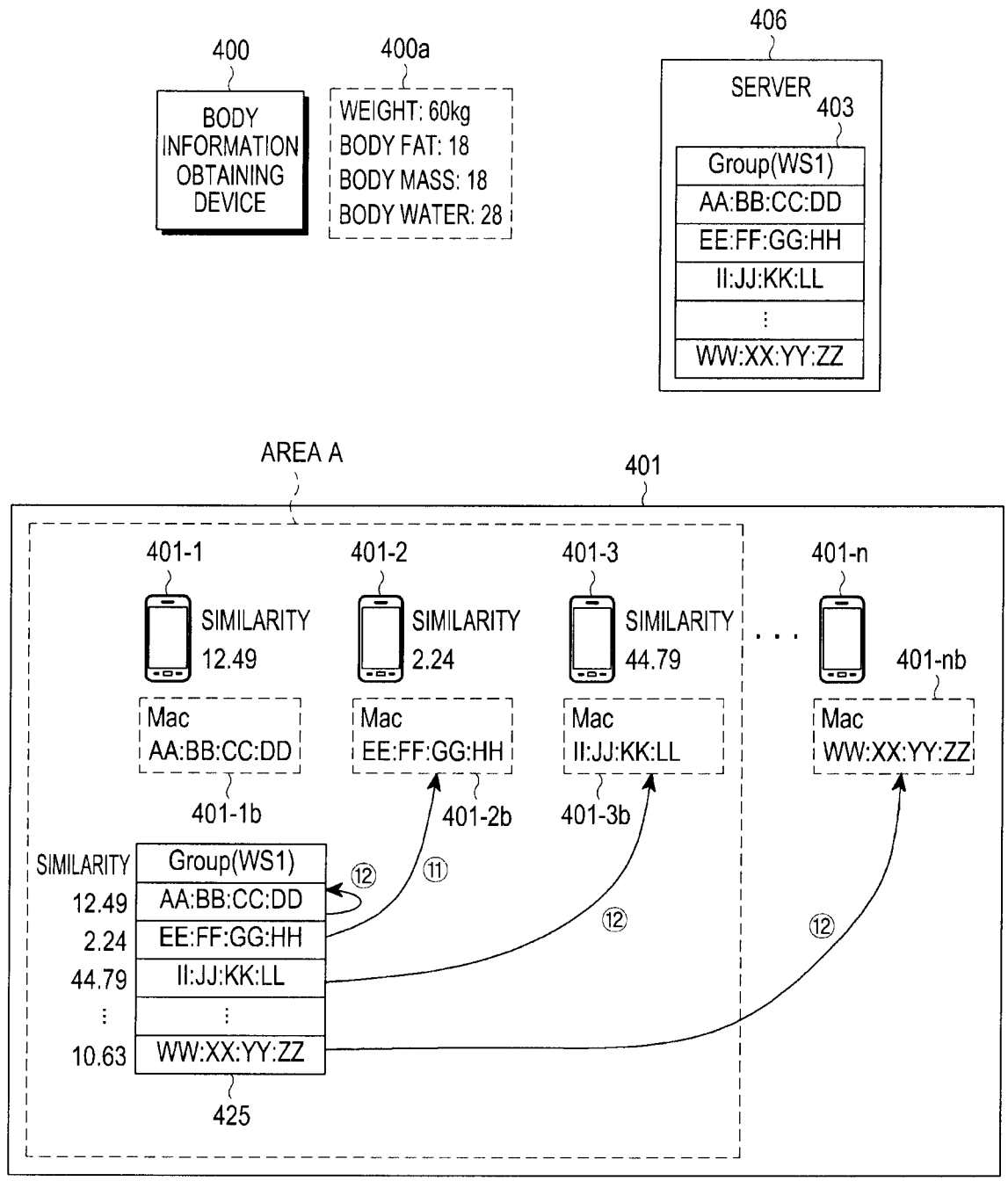

Referring to FIG. 4D, the first electronic device 401-1 may compare the similarity (e.g., 12.49) that the first electronic device 401-1 has calculated with the similarities (e.g., 2.24 and 44.79) received from each of the other electronic devices (e.g., electronic devices 401-2 and 401-3) disposed with the communicable range (area A) of the electronic devices 401-2 to 401-n in the group 425. The first electronic device 401-1 may determine that the electronic device having a lowest similarity (e.g., the second electronic device 401-2) is the user's electronic device, which corresponds to the received body information 400a.

The first electronic device 401-1 may identify the network address information (e.g., MAC address (EE:FF:GG:HH)) 401-2b of the second electronic device 401-2, which has been determined to correspond to the received body information 400a in the group 425, and the first electronic device 401-1 may transmit (⑪) a signal containing a command for storing the received body information 400a to the second electronic device 401-2. The second electronic device 401-2 may cumulatively store the body information 400a received from the first electronic device 401-1 in a memory (e.g., the memory 130 or memory 230) of the second electronic device 401-2. The second electronic device 401-2 may update body information 401-2*a* previously stored in the memory (e.g., the memory 130 or memory 230) with the received body information 400*a*.

The first electronic device 401-1 may identify the network address information of the other electronic devices 401-3 to 401-*n* in the group 425 than the second electronic device 401-2, which has been determined to correspond to the received body information 400*a* in the group 425, and the first electronic device 401-1 may transmit (⑫) a signal containing a command for deleting the received body information 400*a* to each of the other electronic devices 401-3 to 401-*n*. According to the signal (⑫), the first electronic device 401-1 may delete the body information 400*a* temporarily stored or may delete the body information 400*a* without storing. Each of the other electronic devices 401-3 to 401-*n* may delete the body information 400*a* which has temporarily been stored therein or delete the body information 400*a* received from the first electronic device 401-1 without saving according to the signal (⑫) received from the first electronic device 401-1.

FIGS. 5A to 5D are views schematically illustrating a body information managing method in a body information managing system according to an embodiment of the present disclosure. FIGS. 5A to 5D illustrate components related to embodiments of the present disclosure, and other components than the above-listed components may also be included. Referring to FIGS. 5A to 5D, a first electronic device 501-1 of a plurality of electronic devices 501-1 to 501-*n* is assumed to finally be connected to a body information obtaining device 400 for communication, and an electronic device corresponding to body information 500*a* obtained by the body information obtaining device 400 is assumed to a second electronic device 501-2.

Figure 5A:
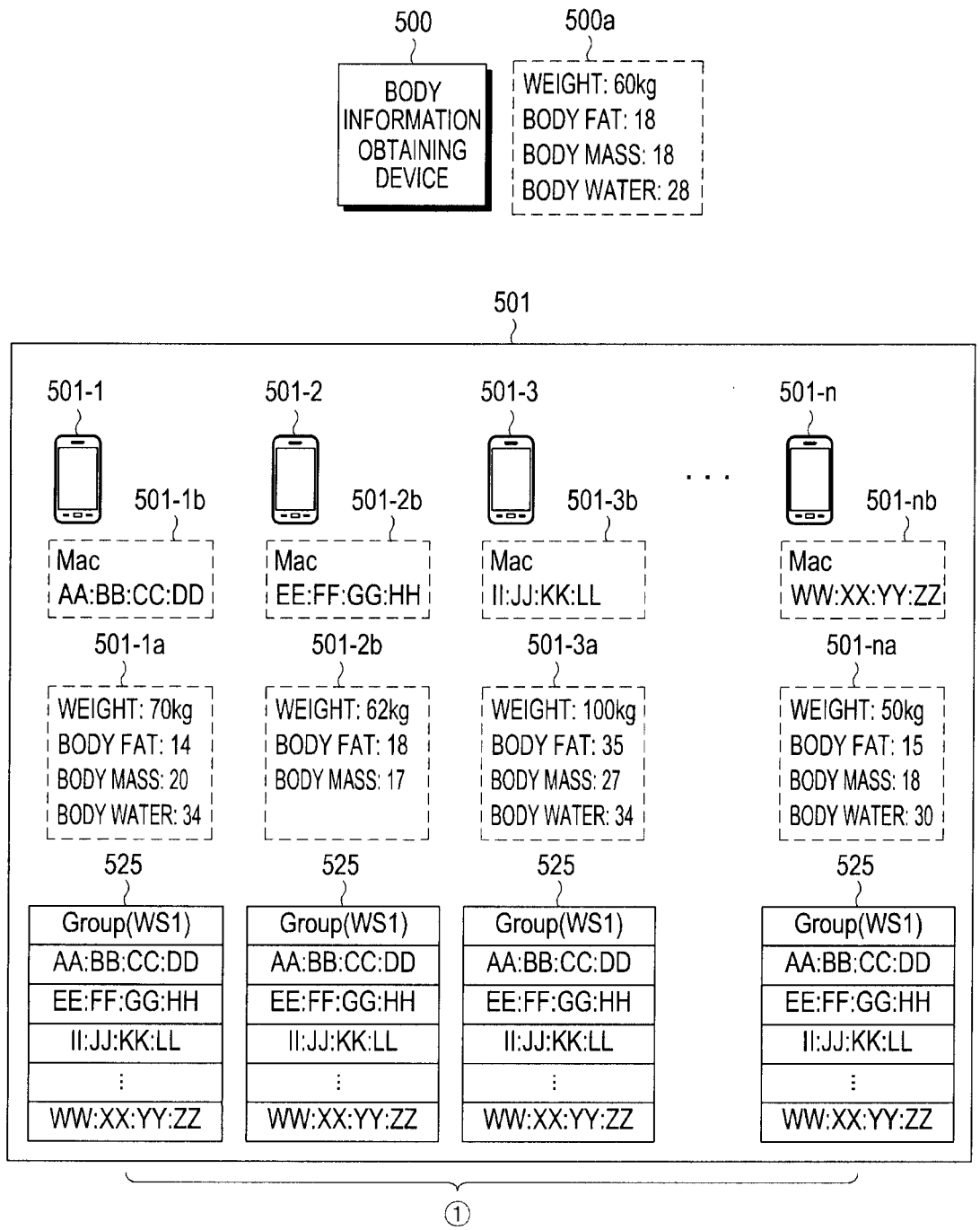
FIG. 5A, FIG. 5B, FIG. 5C and FIG. 5D are views schematically illustrating a body information managing method in a body information managing system according to an embodiment of the present disclosure.

Referring to FIG. 5A, according to an embodiment of the present disclosure, a body information managing system may include a body information obtaining device 500 and a plurality of electronic devices 501-1 to 501-*n*.

The body information obtaining device 500 is the same as the body information obtaining device 400 of FIGS. 4A to 4D, and the description of the body information obtaining device 400 may apply to the body information obtaining device 500.

The plurality of electronic devices 501-1 to 501-*n* may be portable electronic devices, such as smartphones or wearable devices with various functions including communication functionality. According to an embodiment of the present disclosure, the plurality of electronic devices 401-1 to 401-*n* may be at least one user's electronic device(s) sharing the body information obtaining device 500. Each electronic device 501-1 to 501-*n* (which may collectively be denoted with 501) may include the whole or part of each of the electronic devices 401-1 to 401-*n* of FIGS. 4A to 4D. Each of the electronic devices 501-1 to 501-*n* may store information related to at least one electronic device (e.g., electronic devices 501-1 to 501-*n*) registered in a group 525 (e.g., WS1) related to the body information obtaining device 500. For example, each of the electronic devices 501-1 to 501-*n* may receive a request signal for registration information registered in the group 525 related to the body information obtaining device 500 from the at least one of the other electronic devices 501-1 to 501-*n* associated with the body information obtaining device 500. Each of the electronic devices 501-1 to 501-*n*, upon receiving the request signal, may generate a group 525 (e.g., WS1) related to the body information obtaining device 500 and then store and register (①) the corresponding electronic device in the group 525. The group 525 may store information related to the at least one electronic device 501-1 to 501-*n*. For example, each of the electronic devices 501-1 to 501-*n* may send registration request messages for registering them in the group 525 related to the body information obtaining device 500 to the other electronic devices 501-1 to 501-*n*, requesting the other electronic devices to register in the group 525 within each of the electronic device 501-1 to 501-*n*.

According to an embodiment of the present disclosure, the information related to a corresponding electronic device may include at least some of information (e.g., a device identification "ID") for identifying the electronic device, group identification information (e.g., a group ID such as "WS1"), network address information (e.g., a media access control or "MAC" address), body information, information (e.g., a device ID) for identifying the body information obtaining device 500 associated with the electronic device, or a combination thereof.

Figure 5B:
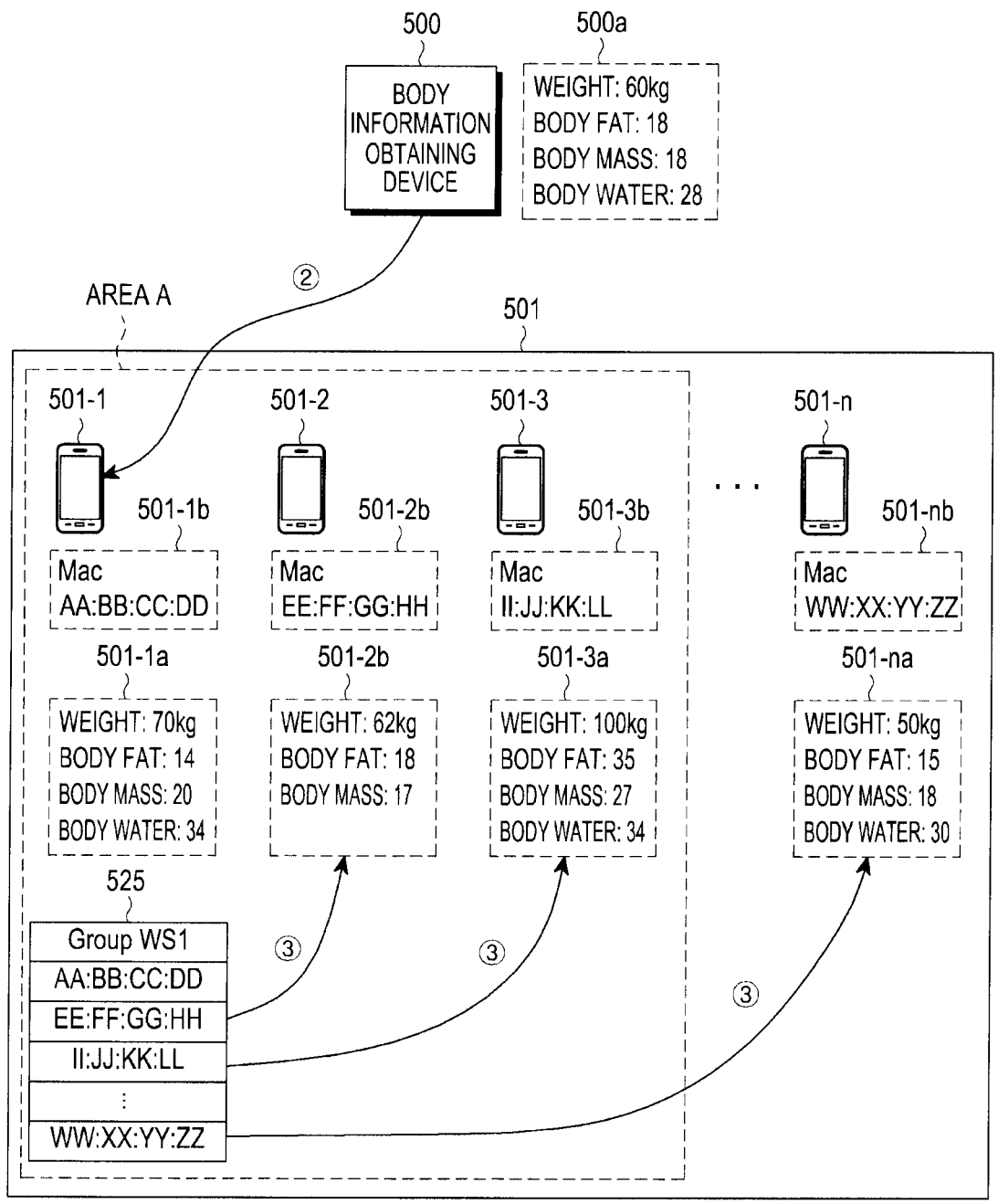

Referring to FIG. 5B, where a first electronic device 501-1 is communicatively coupled to the body information obtaining device 500 and disposed within a communicable range (e.g., area A) thereof, the body information obtaining device 500 may transmit (②) body information 500*a* obtained by the body information obtaining device 500 to the first electronic device 501-1. The body information 500*a* may be information that after obtained by the user has not yet been transmitted to any of the electronic devices 501-1 to 501-*n* included in the group 503.

Upon receiving the body information 500*a* from the body information obtaining device 500, the first electronic device 501-1 may identify information (e.g., network address information (e.g., the MAC addresses 501-2*b* through 501-*nb*)) related to the electronic devices 501-2 to 501-*n* from the group 525 registered and stored within the first electronic device 501-1. The first electronic device 501-1 may transmit (③) the received body information 500*a* to the electronic devices 501-2 to 501-*n* in the group 525 based on the identified information. According to an embodiment of the present disclosure, upon transmission (③), an electronic device (e.g., a n-th electronic device 501-*n*) that is not disposed within the communicable range (area A) with the first electronic device 501-1 may fail to receive the body information 500*a* from the first electronic device 501-1.

Figure 5C:
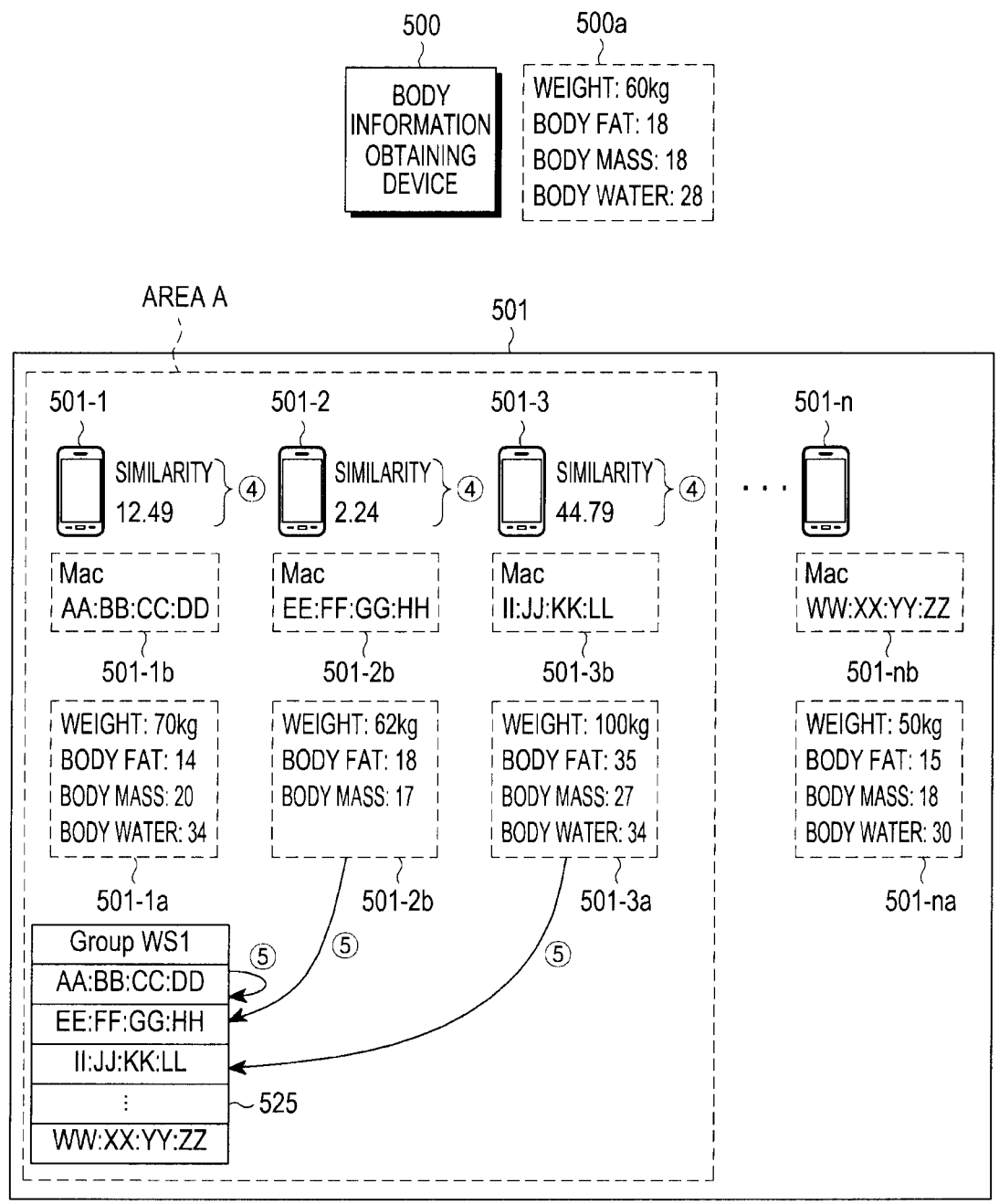

Referring to FIG. 5C, each electronic device (e.g., electronic devices 501-1 to 501-3) disposed within the communicable range (area A) and has received the body information 500*a* may calculate (④) a similarity between the received body information 500*a* and local body information 501-1*a* to 501-3*a* previously stored therein. The previous body information 501-1*a* to 501-3*a* previously stored in each electronic device 501-1 to 501-3 may be the latest body information that the corresponding electronic device has stored.

Each electronic device (e.g., electronic devices 501-1 to 501-3) disposed within the communicable range (area A) among the electronic devices 501-1 to 501-*n* in the group 525 and received the body information 500*a* may transmit (⑤) the calculated similarity to the first electronic device 501-1 based on the first electronic device's network address information 501-1*b*.

Figure 5D:
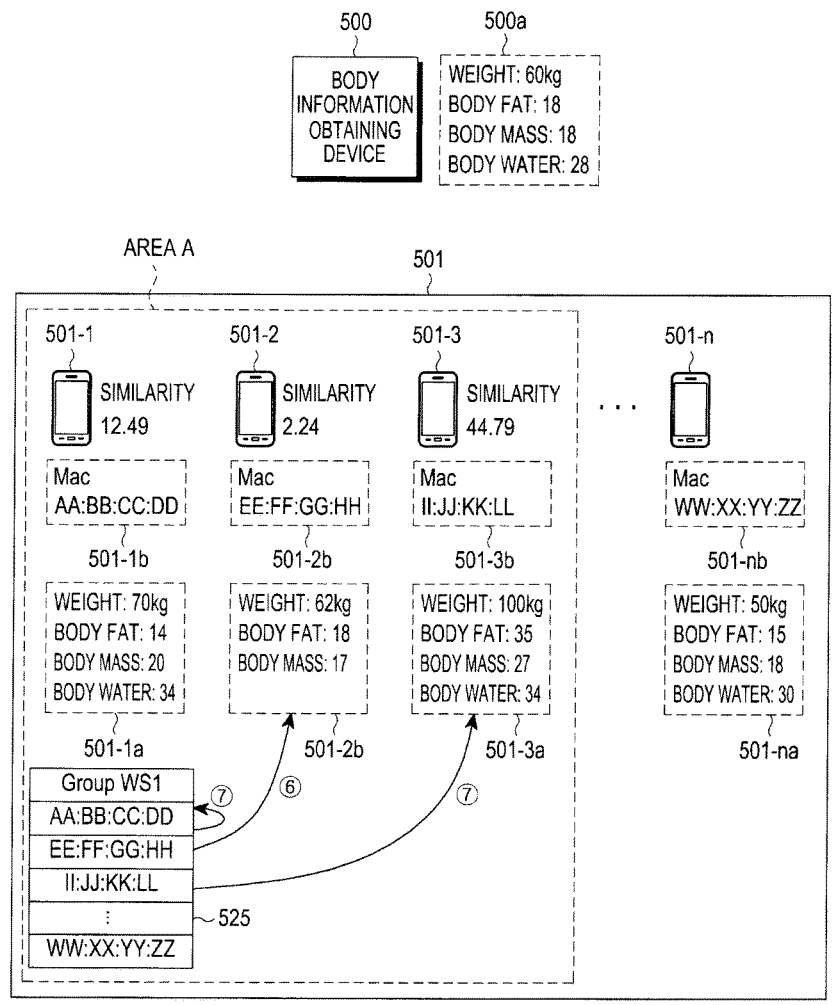

Referring to FIG. 5D, the first electronic device 501-1 may compare the calculated similarity (e.g., 12.49) with the similarity (e.g., 2.24 and 44.79) received from each electronic device (e.g., electronic devices 501-2 and 501-3). The first electronic device 501-1 may determine that the electronic device having the lowest similarity (e.g., the second electronic device 501-2) is the user's electronic device which corresponds to the received body information 500*a*).

The first electronic device 501-1 may identify the network address information (e.g., MAC address EE:FF:GG:HH) 501-2*b* of the second electronic device 501-2, which has been determined to correspond to the received body information 500*a* in the group 525, and the first electronic device 501-1 may transmit (⑥) a signal containing a command for storing the received body information 500*a* to the second electronic device 501-2. The second electronic device 501-2 may cumulatively store the body information 500*a* received from the first electronic device 501-1 in a memory (e.g., the memory 130 or memory 230) of the second electronic device 501-2. The second electronic device 501-2 may update body information 501-2*a* previously stored in the memory (e.g., the memory 130 or memory 230) with the received body information 500*a*.

The first electronic device 501-1 may identify the network address information of the other electronic devices 501-3 to 501-*n* in the group 525 than the second electronic device 401-2, which has been determined to correspond to the received body information 500*a* in the group 525, and the first electronic device 501-1 may transmit (⑦) a signal containing a command for deleting the received body information 500*a* to each of the other electronic devices 501-3 to 501-*n*. According to the signal (⑦), the first electronic device 501-1 may delete the body information 500*a* temporarily stored or may delete the body information 500*a* without storing. Each of the other electronic devices 501-3 to 501-*n* may delete the body information 500*a* which has temporarily been stored therein or delete the body information 500*a* received from the first electronic device 501-1 without saving according to the signal (⑦) received from the first electronic device 501-1.

Figure 6:
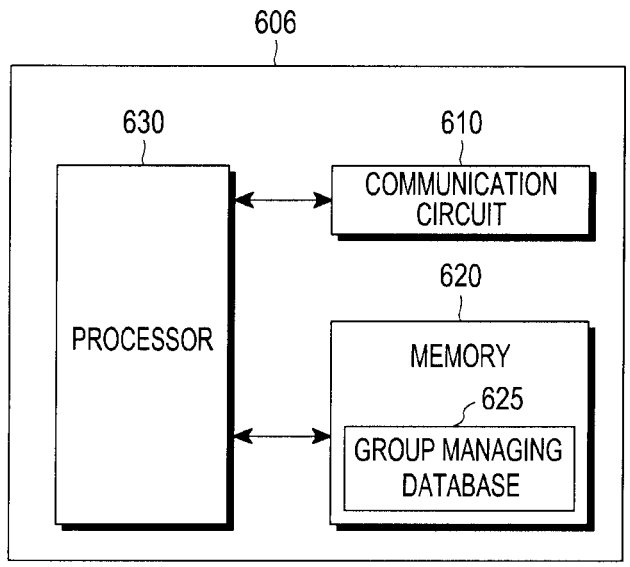
FIG. 6 is a block diagram illustrating a server according to an embodiment of the present disclosure.

FIG. 6 is a block diagram illustrating a server according to an embodiment of the present disclosure.

Referring to FIG. 6, according to an embodiment of the present disclosure, a server 606 may include at least one of a communication circuit 610, a memory 620, or a processor 630. FIG. 6 illustrates components related to embodiments of the present disclosure, and other components than the above-listed components may also be included. For example, the server 606 of FIG. 6 may include the whole or part of the electronic device 101 of FIG. 1, the electronic device 201 of FIG. 2, or the server 406 of FIGS. 4*a* to 4*d*.

The communication circuit 610 may establish a communication link or connection with at least one external electronic device (e.g., the electronic devices 401-1 to 401-*n* of FIGS. 4*a* to 4*d*).

The communication circuit 610 may include the whole or part of, e.g., the communication interface 170 of FIG. 1 or the communication module 220 of FIG. 2. The communication circuit 610 may also be termed a communication unit or communication module, include a communication unit or communication module as part thereof, or may configure a communication unit or communication module.

According to an embodiment of the present disclosure, the communication circuit 610 may provide data based on short-range communication. For example, the communication circuit 610 may establish a communication link with at least one external electronic device (e.g., the electronic devices 401-1 to 401-*n*) connected with a short-range communication-based network. For example, the communication circuit 610 may include at least one of, e.g., a wireless fidelity (Wi-Fi), BlueTooth, near-field communication (NFC), zigbee, z-wave, or global navigation satellite system (GNSS) module or unit.

For example, the memory 620 may store commands or data related to at least one other component of the server 606. The memory 620 may include the whole or part of the memory 130 of FIG. 1 or the memory 230 of FIG. 2.

The memory 620 may store a group (e.g., the group 403 (WS1)) including information related to the at least one external electronic device (e.g., the electronic devices 401-1 to 401-*n*) related to a body information obtaining device (e.g., the body information obtaining device 400). For example, the group 403 may be created as a database that is stored in a group managing database 625 in the memory 620. The information related to the at least one external electronic device (e.g., the electronic devices 401-1 to 401-*n*) may include at least one of, e.g., information (e.g., device ID) for identifying the external electronic device, information (e.g., group ID (e.g., WS1)) for identifying the group where the external electronic device belongs, network address information (e.g., MAC address) of the external electronic device, body information about the user of the external electronic device, information (e.g., ID) for identifying a body information obtaining device (e.g., the body information obtaining device 400) related to the external electronic device, or a combination thereof. The body information may include at least one of, e.g., the user's height, weight, body fat, bone mineral density, skeletal muscle mass, muscle strength, body water level, body fat (e.g., body mass index), basal metabolic rate, biological information, or a combination thereof. The biological information may include, e.g., a biological signal, such as, e.g., an electrocardiography (ECG) signal, an electroencephalogram (EEG) signal, an electrooculogram (EOG) signal, an electrogastrogram (EGG) signal, or an electromyography (EMG) signal, a heart rate, a cardiac cycle, a cardiac cycle standard deviation, a pulse rate, arrhythmia, blood volume impedance, or a stress level. The body information is not limited thereto, and the body information may also include various body-related measurements.

The memory 620 may store body information obtained by the body information obtaining device 400, which is received from one of the at least one external electronic device 401-1 to 401-*n*. The memory 620 may store similarities calculated for the at least one external electronic device 401-1 to 401-*n* using the received body information and the body information of the at least one external electronic device 401-1 to 401-*n* (hereinafter, the body information of each external electronic device 401-1 to 401-*n* is denoted 'prior body information') and temporary computational values that are generated during the course of calculating the similarities.

The processor 630 may overall control the server 606. For example, the processor 630 may generate the group (e.g., the group 403) including information related to the at least one external electronic device 401-1 to 401-*n* related to the body information obtaining device 400. The processor 630 may receive a request for registration in the group 430 from the at least one external electronic device 401-1 to 401-*n*. For example, the processor 630 may receive a registration request message including information related to the external electronic device from the external electronic device 401-1 to 401-*n* related to the body information obtaining device 400. In response to the registration request, the processor 630 may register a corresponding external electronic device in the group 403. For example, in response to the request for registration in the group 403 from the at least one external electronic device 401-1 to 401-*n*, the processor 630 may obtain information related to the corresponding external electronic device from the registration request message. The processor 630 may register the external electronic device by storing the obtained information in the group 403 generated in the memory 20 (e.g., the group managing database 625).

The processor 630 may receive the body information obtained by the body information obtaining device 400 from one of the at least one external electronic device 401-1 to 401-*n*. For example, the body information obtained by the body information obtaining device 400 may be transmitted to an external electronic device (e.g., a first external electronic device 401-1) of the at least one external electronic device 401-1 to 401-*n* in the group related to the body information obtaining device 400, that is finally connected with the body information obtaining device 400 and that is positioned within a short-range communicable range (e.g., area A), and the final-connected external electronic device 401-1 may receive the body information and transmit the body information to the server 606. By so doing, the processor 630 may receive the biological information from the external electronic device 401-1 finally connected with the body information obtaining device 400.

Upon receiving the body information obtained by the body information obtaining device 400 from one (e.g., the first external electronic device 401-1) of the at least one external electronic device 401-1 to 401-*n*, the processor 210 may identify information related to the at least one external electronic device 401-1 to 401-*n* from the group 403 where the external electronic device 401-1 belongs. The processor 630 may calculate similarities for the at least one external electronic device 401-1 to 401-*n* based on the received body information and the information related to the at least one external electronic device 401-1 to 401-*n*. For example, the processor 630 may calculate distance-based similarities between the received body information and the body information of each external electronic device among pieces of information related to the at least one external electronic device 401-1 to 401-*n*. In this disclosure, the distance-based similarity may be an Euclidean distance-based similarity in body information.

The Euclidean distance-based similarity may be calculated based on Equation 1 below:

$$\text{Similarity} = \sqrt{(Weight_p - Weight_q)^2 + (Bodyfat_p - Bodyfat_q)^2 + (Bonemineraldensity_p - Bonemineraldensity_q)^2 + \ldots + (Basemetabolicrate_p - Basemetabolicrate_q)^2}$$

[Equation 1]

Here, p refers to the body information received from the body information obtaining device 400 or 500: p={weight, body fat, bone mineral density, skeletal muscle mass, muscle strength, body water, body mass (BMI), . . . , basal metabolic rate}. q refers to the body information finally stored in the external electronic device: q={weight, body fat, bone mineral density, skeletal muscle mass, muscle strength, body water, body mass (BMI), . . . , basal metabolic rate}.

p and q, however, are not limited thereto, and they may include other various types of body information. As p and q include more parameters for the body information, i.e., Equation 1 is higher order, the accuracy of similarity may be enhanced.

For example, the similarities calculated for the at least one external electronic device 401-1 to 401-*n* in the group 403 (WS1) are shown in Table 1 below.

TABLE 1

| Network address | Similarity |
|---|---|
| AA:BB:CC:DD | $\sqrt{(60-70)^2 + (18-14)^2 + (18-20)^2 + (28-34)^2} = 12.49$ |
| EE:FF:GG:HH | $\sqrt{(60-62)^2 + (18-18)^2 + (18-17)^2} = 2.24$ |
| II:JJ:KK:LL | $\sqrt{(60-100)^2 + (18-35)^2 + (18-27)^2 + (28-34)^2} = 44.79$ |
| . | . |
| . | . |
| . | . |
| WW:XX:YY:ZZ | $\sqrt{(60-50)^2 + (18-15)^2 + (18-18)^2 + (28-30)^2} = 10.63$ |

From Table 1 above, the network address and similarity of each of the at least one external electronic device 401-1 to 401-*n* in the group 403 (WS1) may be known. For example, the received body information may be represented as follows: p={weight, body fat, body mass, basal metabolic rate}={60, 18, 18, 28}. In this case, when the body information related to the first external electronic device 401-1 of the network address "AA:BB:CC:DD" is represented as q={weight, body fat, body mass, basal metabolic rate}={70, 14, 20, 34}, the similarity for the first external electronic device 401-1 calculated based on Equation 1 may be 12.49. When the body information related to the second external electronic device 401-2 of the network address "EE:FF:GG:HH" is represented as q={weight, body fat, body mass}={62, 18, 17}, the similarity for the second external electronic device 401-2 calculated based on Equation 1 may be 2.24. When the body information related to the third external electronic device 401-3 of the network address "II:JJ:KK:LL" is represented as q={weight, body fat, body mass, body water level}={100, 35, 37, 34}, the similarity for the third external electronic device 401-3 calculated based on Equation 1 may be 44.79. When the body information related to the last external electronic device 401-*n* of the network address "WW:XX:YY:ZZ" is represented as q={weight, body fat, body mass, body water level}={50, 15, 18, 30}, the similarity for the n-th external electronic device 401-*n* calculated based on Equation 1 may be 10.63.

The processor 630 may determine that the external electronic device (e.g., the second external electronic device 401-2) corresponding to the minimum similarity (e.g., 2.24) of the similarities for the at least one external electronic device 401-1 to 401-*n* in the group 403 (WS1) corresponds to the received body information. The processor 630 may store the received body information in the determined external electronic device (e.g., the second external electronic device 401-2). The processor 630 may identify the network address (e.g., EE:FF:GG:HH) of the determined external electronic device (e.g., the second external electronic device 401-2) and transmit the received body information to the determined external electronic device (e.g., the second external electronic device 401-2).

The processor 630 may receive an information request message for requesting the network address information of the remaining external electronic devices (e.g., the external electronic devices 401-2 to 401-*n*) in the group 403 from the external electronic device (e.g., the first external electronic device 401-1) finally connected to the body information obtaining device 400 for communication among the at least one external electronic device 401-1 to 401-*n* registered in the group 403. In response to the information request, the processor 630 may load the information of the remaining external electronic devices 401-2 to 401-*n* from the memory 620 and transmit a response message containing the network address information of the remaining external electronic devices 401-2 to 401-*n* to the requesting external electronic device (e.g., the first external electronic device 401-1).

According to an embodiment of the present disclosure, an electronic device (e.g., the server 606) may include a communication circuit 610, a memory 620 storing a group (e.g., the group 403) including information related to at least one external electronic device related to an external body information obtaining device (e.g., the body information obtaining device 400), and a processor 630 configured to receive body information obtained by the external body information obtaining device 400 from one of the at least one external electronic device (e.g., the electronic devices 401-1 to 401-*n*) in the group 403, determine an external electronic device corresponding to the received body information 400*a* among the at least one external electronic device 401-1 to 401-*n* based on the received body information 400*a* and the information related to the at least one external electronic device 401-1 to 401-*n*, and transmit the received body information 400*a* to the determined external electronic device.

According to an embodiment of the present disclosure, the processor 630 may be configured to determine the external electronic device corresponding to the received body information 400*a* among the at least one external electronic device based on a similarity between the received body information 400*a* and prior body information of each external electronic device among pieces of the information related to the at least one external electronic device 401-1 to 401-*n*.

According to an embodiment of the present disclosure, the processor 630 may be configured to calculate a distance-based similarity between the received body information 400*a* and the prior body information of each external electronic device 401-1 to 401-*n* and to determine that an external electronic device having a minimum similarity corresponds to the received body information 400*a*.

According to an embodiment of the present disclosure, the distance-based similarity may be an Euclidean distance-based similarity.

According to an embodiment of the present disclosure, the processor 630 may be configured to update the memory 620 to store the received body information in the information related to the determined external electronic device and to transmit the received body information to the determined external electronic device based on network address information among pieces of information related to the determined external electronic device.

According to an embodiment of the present disclosure, the processor 630 may be configured to, upon receiving a request for information related to at least one other external electronic device 401-2 to 401-*n* in the group other than one (e.g., the electronic device 401-1) of the at least one external electronic device 401-1 to 401-*n*, transmit the information related to the at least one other external electronic device 201-2 to 401-*n* in the group to a corresponding external electronic device 401-1.

Figure 7:
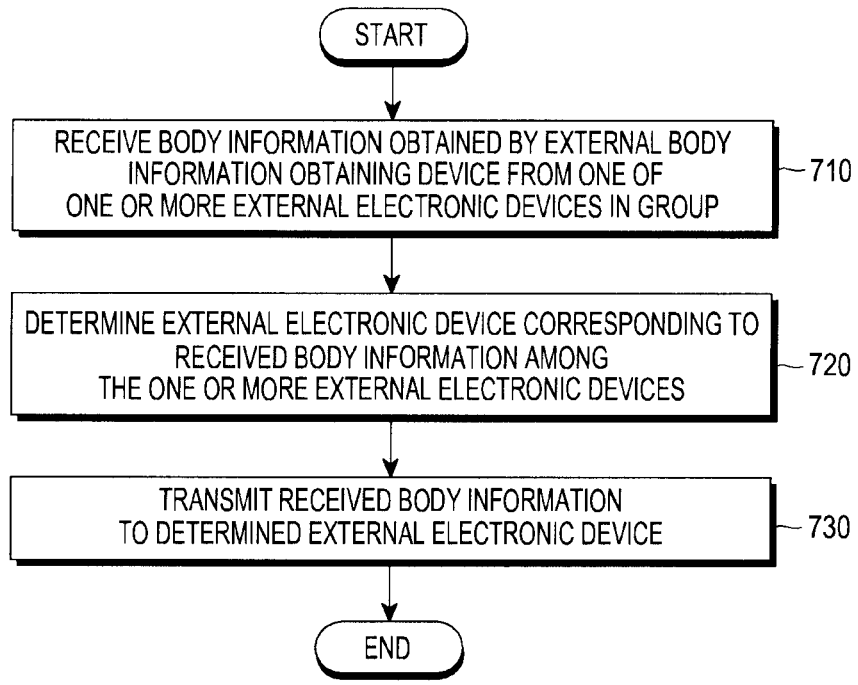
FIG. 7 is a flowchart illustrating a method for managing body information by a server according to an embodiment of the present disclosure.

FIG. 7 is a flowchart illustrating a method for managing body information by a server according to an embodiment of the present disclosure. The body information managing method may be performed by at least one of a server (e.g., the server 606) or a processor (e.g., the processor 630) of the server.

In operation 710, the server may receive body information obtained by an external body information obtaining device (e.g., 400 or 500) from one of one or more external electronic devices in the group (e.g., the group 403 "WS1") including information related to the at least one external electronic device (e.g., the external electronic device 401-1 to 401-*n*) related to the external body information obtaining device.

According to an embodiment of the present disclosure, the server may receive the body information obtained by the external body information obtaining device from an external electronic device (e.g., the first external electronic device) that is communicatively coupled with the external body information obtaining device among the one or more external electronic devices in the group disposed within a short-range communicable range from the external body information obtaining device.

In operation 720, the server may determine one particular external electronic device corresponding to the received body information from among the one or more external electronic devices 401-1 to 401-*n*, based on the body information of each external electronic device among pieces of information related to the at least one external electronic device and the received body information.

According to an embodiment of the present disclosure, the server may calculate distance-based similarities using the received body information and the body information of each external electronic device. The server may determine that the external electronic device having the lowest similarity of the calculated distance-based similarities corresponds to the received body information.

According to an embodiment of the present disclosure, the distance-based similarities may be Euclidean distance-based body information similarities.

In operation 730, the server may transmit the received body information to the external electronic device (e.g., the second external electronic device 401-2) determined to correspond to the received body information.

For example, the server may load the network address information (e.g., the network address information (EE:FF:GG:HH)) of the external electronic device (e.g., the second external electronic device) determined to correspond to the received body information from the group stored in the group managing database 625 inside the memory (e.g., the memory 620) and transmit the received body information to the determined external electronic device (e.g., the second external electronic device) based on the loaded network address information.

The server may update the memory to store the received body information in the information related to the determined external electronic device (e.g., the second external electronic device).

Figure 8:
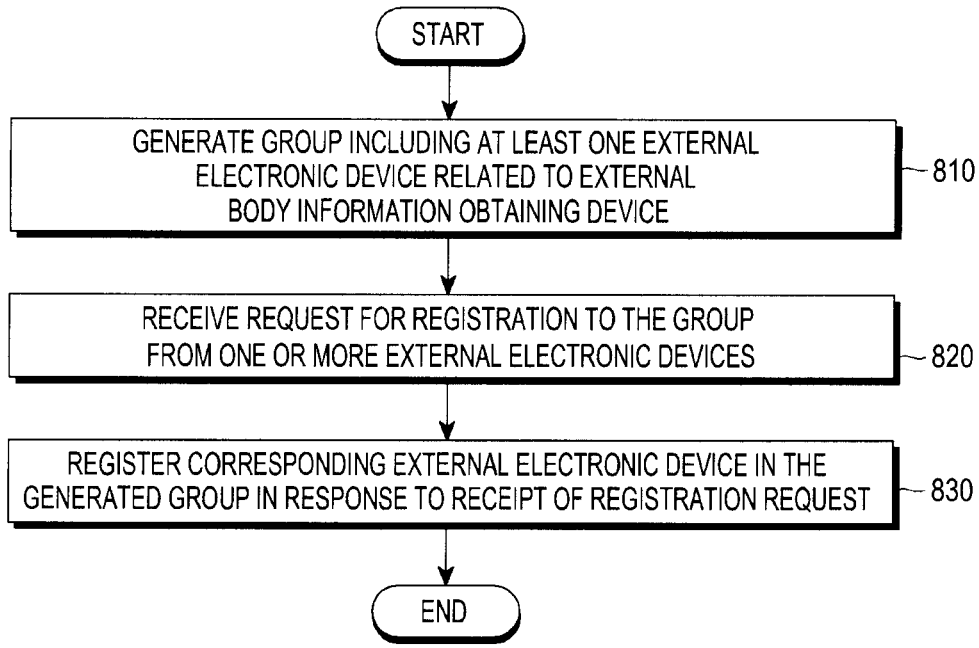
FIG. 8 is a flowchart illustrating a method for managing body information by a server according to an embodiment of the present disclosure.

FIG. 8 is a flowchart illustrating a method for managing body information by a server according to an embodiment of the present disclosure. The body information managing method shown in FIG. 8 is provided to describe a method for registering at least one external electronic device related to an external body information obtaining device in the group 403 (WS1) stored in the server, and the method may be performed by at least one of a server (e.g., the server 606) or a processor (e.g., the processor 630) of the server.

In operation 810, the server may generate a group (e.g., the group 403 "WS1") including at least one external electronic device (e.g., the external electronic device 401-1 to 401-*n*) related to the external body information obtaining device (e.g., the external body information obtaining device 400 or 500). For example, the server may generate the group including information related to the at least one external electronic device (e.g., the external electronic device 401-1 to 401-*n*) related to the external body information obtaining device in the group managing database 625 of the memory (e.g., the memory 620) of the server.

In operation 820, the server may receive a request for registration in the group from the at least one external electronic device. For example, the server may receive a registration request message including the information related to the external electronic device from the at least one external electronic device related to the external body information obtaining device. The information related to the at least one external electronic device may include at least one of, e.g., information (e.g., device ID) for identifying the external electronic device, information (e.g., group ID (e.g., WS1)) for identifying the group where the external electronic device belongs, network address information (e.g., MAC address) of the external electronic device, body information about the user of the external electronic device, information (e.g., device ID) for identifying the external body information obtaining device related to the external electronic device, or a combination thereof. The body information may include at least one of, e.g., the user's height, weight, body fat, bone mineral density, skeletal muscle mass, muscle strength, body water level, body fat (e.g., body mass index), basal metabolic rate, biological information, or a combination thereof. The biological information may include, e.g., a biological signal, such as, e.g., an electrocardiography (ECG) signal, an electroencephalogram (EEG) signal, an electrooculogram (EOG) signal, an electrogastrogram (EGG) signal, or an electromyography (EMG) signal, a heart rate, a cardiac cycle, a cardiac cycle standard deviation, a pulse rate, arrhythmia, blood volume impedance, or a stress level.

In operation 830, the server may register the external electronic device in the generated group in response to a receipt of the registration request. For example, the server may obtain the information related to the external electronic device from the registration request message. The server may store the obtained information in the group generated in the memory of the server to update the information. For example, in the group related to the external body information obtaining device, the information related to the at least one external electronic device may be stored in the form of a lookup table in the group managing database inside the memory of the server.

When the registration of the device in the group is complete in response to the registration request, the server may transmit a registration response message indicating that the corresponding electronic device has been registered in the group to the external electronic device.

Figure 9:
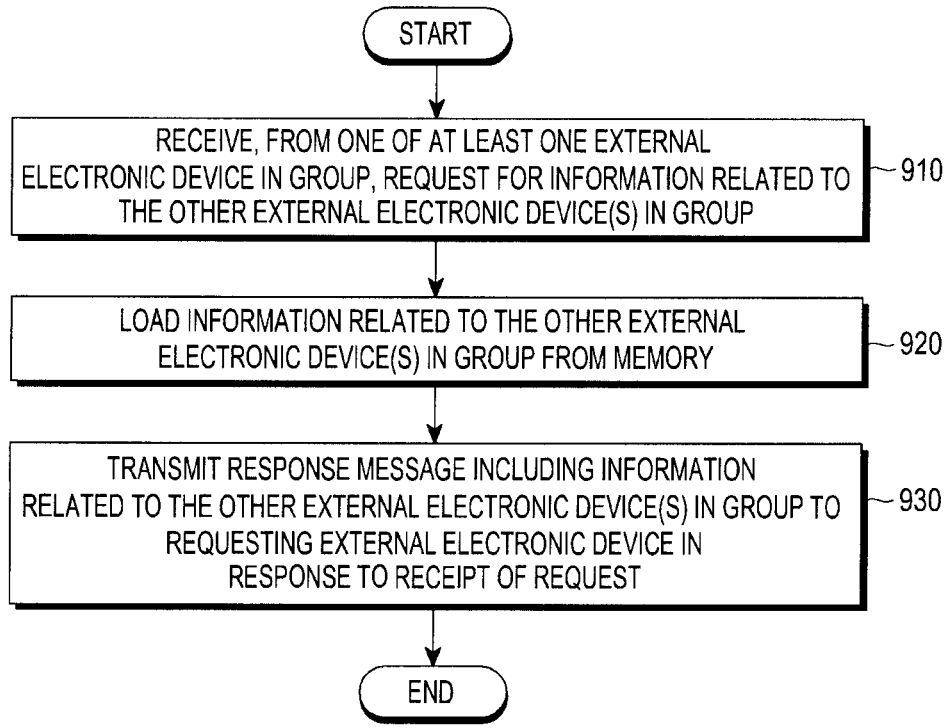
FIG. 9 is a flowchart illustrating a method for managing body information by a server according to an embodiment of the present disclosure.

FIG. 9 is a flowchart illustrating a method for managing body information by a server according to an embodiment of the present disclosure. The body information managing method may be performed by at least one of a server (e.g., the server 606) or a processor (e.g., the processor 630) of the server.

In operation 910, the server may receive, from one (e.g., the first electronic device 401-1) of the at least one external electronic device in the group (e.g., the group 403 (WS1)) including the information related to the at least one external electronic device (e.g., the electronic devices 401-1 to 401-*n*) related to the external body information obtaining device (e.g., the body information obtaining device 400), a request for information related to the other external electronic devices (e.g., the electronic devices 401-2 to 401-*n*) in the group.

According to an embodiment of the present disclosure, the server may receive an information request message to request the information related to the other external electronic devices in the group from the external electronic device (e.g., the first electronic device 401-1) finally connected with the external body information obtaining device for communication among the at least one external electronic device that is positioned within a short-range communication range from the external body information obtaining device among the at least one external electronic device registered in the group.

According to an embodiment of the present disclosure, the information related to the other external electronic devices in the group may be network address information.

In operation 920, the server, upon receiving the request, may load the information related to the other external electronic devices from the group managing database 625 in the memory (e.g., the memory 620).

According to an embodiment of the present disclosure, the server may load the network address information among pieces of the information related to the other external electronic devices in the group from the group managing database of the memory.

In operation 930, the server may transmit a response message including the loaded information related to the other external electronic devices to the requesting external electronic device (e.g., the first electronic device 401-1) in response to a receipt of the information request.

According to an embodiment of the present disclosure, the server may transmit a response message including network information among pieces of the information related to the other external electronic devices in the group which are loaded from the memory to the requesting external electronic device (e.g., the first electronic device 401-1).

According to an embodiment of the present disclosure, there is provided a storage medium storing commands, the commands configured to be executed by at least one processor of an electronic device to enable the at least one processor to perform at least one operation. The at least one operation may include storing a group including information related to at least one external electronic device related to an external body information obtaining device, receiving body information obtained by the external body information obtaining device from one of the at least one external electronic device in the group, determining an external electronic device corresponding to the received body information among the at least one external electronic device based on the received body information and the information related to the at least one external electronic device, and transmitting the received body information to the determined external electronic device.

According to an embodiment of the present disclosure, determining the external electronic device corresponding to the received body information may include determining the external electronic device corresponding to the received body information among the at least one external electronic device based on a similarity between the received body information and prior body information of each external electronic device among pieces of the information related to the at least one external electronic device.

According to an embodiment of the present disclosure, determining the external electronic device corresponding to the received body information may include calculating a distance-based similarity between the received body information and the prior body information of each external electronic device and determining that an external electronic device having a minimum similarity corresponds to the received body information.

According to an embodiment of the present disclosure, transmitting the received body information to the determined external electronic device may include updating the memory to store the received body information in the information related to the determined external electronic device and transmitting the received body information to the determined external electronic device based on network address information among pieces of information related to the determined external electronic device.

According to an embodiment of the present disclosure, the at least one operation may further include, upon receiving a request for information related to at least one other external electronic device in the group other than one of the at least one external electronic device, transmitting the information related to the at least one other external electronic device in the group to a corresponding external electronic device.

Figure 10:
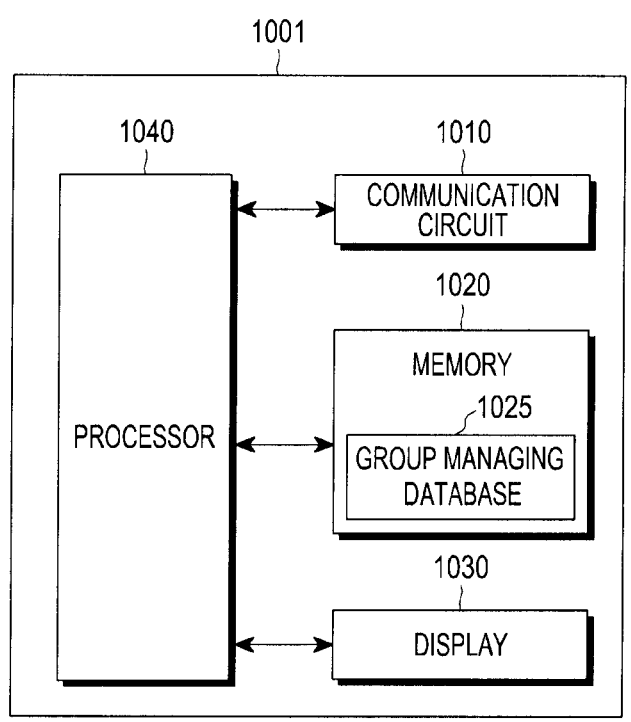
FIG. 10 is a block diagram illustrating an electronic device according to an embodiment of the present disclosure.

FIG. 10 is a block diagram illustrating an electronic device according to an embodiment of the present disclosure.

Referring to FIG. 10, according to an embodiment of the present disclosure, an electronic device 1001 may include a communication circuit 1010, a memory 1020, a display 1030, and a processor 1040. FIG. 10 illustrates components related to embodiments of the present disclosure, and other components than the above-listed components may also be included. For example, the electronic device 1001 of FIG. 10 may include the whole or part of the electronic device 101 of FIG. 1, the electronic device 201 of FIG. 2, the electronic device 401 of FIGS. 4a to 4d, or the electronic device 501 of FIGS. 5a to 5d. In this disclosure, the electronic device 1001 is assumed to be the electronic device (e.g., the first electronic device 401-1 or 501-1) finally connected with the external body information obtaining device 400 or 500 for communication among the at least one electronic device 401-1 to 401-n of FIGS. 4a to 4d or the at least one electronic device 501-1 to 501-n of FIGS. 5a to 5d.

The communication circuit 1010 may establish a communication link with at least one external electronic device (e.g., the electronic devices 401-2 to 401-n of FIGS. 4a to 4d, the electronic devices 501-2 to 501-n of FIGS. 5a to 5d, the body information obtaining device 400 or 500, or the server 606) and receive predetermined information from the external electronic device (e.g., the electronic devices 401-2 to 401-n or 501-2 to 501-n, the body information obtaining device 400 or 500, or the server 606).

The communication circuit 1010 may include the whole or part of, e.g., the communication interface 170 of FIG. 1 or the communication module 220 of FIG. 2. The communication circuit 1010 may also be termed a communication unit or communication module, include a communication unit or communication module as part thereof, or may configure a communication unit or communication module.

According to an embodiment of the present disclosure, the communication circuit 1010 may provide data based on short-range communication. For example, the communication circuit 1010 may establish a communication link with at least one external electronic device (e.g., the electronic devices 401-2 to 401-n or 502-1 to 501-n), a body information obtaining device 400 or 500, or server 606 connected with a short-range communication-based network. For example, the communication circuit 1010 may include at least one of, e.g., a wireless fidelity (Wi-Fi), BlueTooth, near-field communication (NFC), zigbee, z-wave, or global navigation satellite system (GNSS) module or unit.

The communication circuit 1010 may receive information from at least one external electronic device (e.g., the electronic devices 401-2 to 401-n or 501-1 to 501-n), a body information obtaining device 400 or 500, or server 606. For example, as the information, the body information (e.g., the body information 400a or 500a) obtained by the body information obtaining device 400 or 500 may be received, or information related to the at least one external electronic device (e.g., the electronic devices 401-2 to 401-n) in the group (e.g., the group 403) related to the external body information obtaining device 400 or 500 registered in the server 606 may be received from the server 606.

The display 1030 may be disposed between a first surface (e.g., a front surface of the electronic device 1001) that faces in a first direction of the electronic device 1001 and a second surface (e.g., a rear surface of the electronic device 1001) that faces in a second direction which is an opposite direction of the first direction. The top of the display 1030 may be displayed through the first surface. The display 1030 may be large enough to take up a majority of the first surface of the electronic device 1001.

According to an embodiment, the display 1030 may include a liquid crystal display (LCD) or active matrix organic light emitting diode (AMOLED) panel. The display 1030 may display various images according to services and/or execution of an application.

For example, the display 1030 may display body information corresponding to the user of the electronic device 1001 among pieces of information obtained by the body information obtaining device 400 or 500. The body information may include at least one of, e.g., the user's height, weight, body fat, bone mineral density, skeletal muscle mass, muscle strength, body water level, body fat (e.g., body mass index), basal metabolic rate, biological information (e.g., heartrate or stress level), or a combination thereof. The biological information may include, e.g., a biological signal, such as, e.g., an electrocardiography (ECG) signal, an electroencephalogram (EEG) signal, an electrooculogram (EOG) signal, an electrogastrogram (EGG) signal, or an electromyography (EMG) signal, a heart rate, a cardiac cycle, a cardiac cycle standard deviation, a pulse rate, arrhythmia, blood volume impedance, or a stress level. The body information is not limited thereto, and the body information may also include various body-related measurements.

For example, the memory 1020 may store commands or data related to at least one other component of the electronic device 501. The memory 1020 may include the whole or part of the memory 130 of FIG. 1 or the memory 230 of FIG. 2. The memory 1020 may store the user's body information obtained by the body information obtaining device 400 or 500. The body information may be stored cumulatively to the prior body information, or when new body information is received, the prior body information may be updated with the new body information.

The memory 1020 may store the similarity calculated between the prior body information and the newly received body information or temporary computational values used to calculate the similarity. The memory 1020 may also store the similarity between the newly received body information and the prior body information stored in each external electronic device that is received from each of at least one external electronic device 401-2 to 401-n or 501-2 to 501-n in the group 403 WS1.

The memory 1020 may store a group (e.g., the group 425 or 525 (WS1)) including information related to the at least one external electronic device 401-2 to 401-n or 501-2 to 502-n related to the body information obtaining device 400 or 500. For example, the information related to the at least one external electronic device 401-2 to 401-n or 501-2 to 501-n in the group 425 or 525 may be created as a database and stored in the group managing database 1025 in the memory 1020. The information related to the at least one external electronic device (e.g., the electronic devices 401-2 to 401-*n* or 501-2 to 501-*n*) in the group 425 or 525 may include at least one of, e.g., information (e.g., device ID) for identifying the external electronic device, information (e.g., group ID (e.g., WS1)) for identifying the group where the external electronic device belongs, network address information (e.g., MAC address) of the external electronic device, body information about the user of the external electronic device, information (e.g., ID) for identifying the body information obtaining device 400 or 500 related to the external electronic device, or a combination thereof.

The processor 1040 may send a request for registration in the group (e.g., group 403) related to the external body information obtaining device (e.g., the body information obtaining device 400) to the server 606. For example, the processor 1040 may transmit a registration request message including information related to the electronic device 1001 to the server 606. The information related to the electronic device 1001 may include at least one of information (e.g., device ID) for identifying the electronic device 1001, information (e.g., group ID (e.g., WS1)) for identifying the group where the electronic device 1001 belongs, network address information (e.g., MAC address) of the electronic device 1001, body information about the user of the electronic device 1001, information (e.g., ID) for identifying a body information obtaining device (e.g., the body information obtaining device 400) related to the electronic device 1001, or a combination thereof. The server 606 may register the electronic device 1001 by receiving the registration request message containing the information related to the electronic device 1001 and storing the information related to the electronic device 1001 in the group 403 stored in the server 606. In response to the registration request, the processor 1040 may receive, from the server 606, a response message indicating that the electronic device 1001 has been registered in the group 403 (WS1).

The processor 1040 may receive the body information (e.g., body information 400*a* or body information 500*a*) obtained by the external body information obtaining device 400 or 500 from the external body information obtaining device 400 or 500. For example, where the electronic device 1001 is one positioned within a short-range communicable range from the external body information obtaining device 400 or 500 and finally connected with the external body information obtaining device 400 or 500 for communication, the processor 1040 may receive the body information obtained by the external body information obtaining device 400 or 500 from the external body information obtaining device 400 or 500.

Upon receiving the body information from the external body information obtaining device 400 or 500, the processor 1040 may transmit the received body information to the server 606.

The processor 1040 may receive one of a command for storing or a command for deleting the received body information in response to the body information received from the server 606 according to the determination of the server 606.

The processor 1040, upon receiving the command for storing the body information from the server 606, may store the received body information in the memory 1020. For example, the processor 1040 may cumulatively store the received body information in the memory 1020 or update the prior body information which used to be stored in the electronic device 1001 with the received body information.

The processor 1040, upon receiving the command for deleting the received body information from the server 606, may delete the received body information from the memory 1020.

According to an embodiment of the present disclosure, absent the server 606, a group (e.g., 425 or 525) may be generated in each of the electronic device 1001 and the at least one external electronic device 401-2 to 401-*n* or 501-2 to 501-*n*.

For example, the processor 1040 may generate a group (e.g., the group 425 or 525 (WS1)) related to the external body information obtaining device 400 or 500 in the memory 1020. For example, the processor 1040 may generate the group 425 or 525 including the electronic device 1001 and the at least one external electronic device (e.g., the external electronic device 401-2 to 401-*n* or 501-2 to 501-*n*) related to the external body information obtaining device 400 or 500 in the group managing database 1025 inside the memory 1020 of the electronic device 1001.

The processor 1040 may receive a request for registration in the group 425 or 525 from the at least one external electronic device 401-2 to 401-*n* or 501-2 to 501-*n*. For example, the processor 1040 may receive a registration request message including information related to the external electronic device from the external electronic device 401-2 to 401-*n* or 501-2 to 501-*n* related to the external body information obtaining device 400 or 500. The information related to the at least one external electronic device may include at least one of, e.g., information (e.g., device ID) for identifying the external electronic device, information (e.g., group ID (e.g., WS1)) for identifying the group where the external electronic device belongs, network address information (e.g., MAC address) of the external electronic device, body information about an user of the external electronic device, information (e.g., device ID) for identifying the external body information obtaining device related to the external electronic device, or a combination thereof.

In response to the registration request, the processor 1040 may register the corresponding external electronic device in the group 425 or 525 generated. For example, the processor 1040 may obtain the information related to the external electronic device from the registration request message. The processor 1004 may store the obtained information in the memory 1020 of the electronic device 1001 to update the group 425 or 525 (WS1). For example, the group 425 or 525 (WS1) related to the external body information obtaining device 400 or 500 may be created as a database as the information related to the at least one external electronic device 401-2 to 401-*n* or 501-2 to 501-*n* is stored in the group managing database 1025 inside the memory 1020 of the electronic device 1001. The group 425 or 525 related to the external body information obtaining device 400 or 500 may also be created in each of the at least one external electronic device 401-2 to 401-*n* or 501-2 to 501-*n* and may be stored in the memory of the external electronic device.

Where the server 606 is not provided, the processor 1040, upon receipt of the body information obtained by the external body information obtaining device 400 or 500 from, e.g., the external body information obtaining device 400 or 500, may transmit the received body information to the at least one external electronic device 401-2 to 401-*n* or 501-2 to 501-*n* in the group 425 or 525 based on the network address information among pieces of information related to the at least one external electronic device 401-2 to 401-*n* or 501-2 to 501-*n* in the group 425 or 525.

The processor 1040 may perform control so that the received body information is stored in the device corresponding to the received body information among the at least one external electronic device 401-2 to 401-*n* or 501-2 to 501-*n* and the electronic device 1001 based on the received body information and the prior body information stored in each of the at least one external electronic device 401-2 to 401-*n* or 501-2 to 501-*n* and the electronic device 1001. The processor 1040 may determine the device corresponding to the received body information among the at least one external electronic device 401-2 to 401-*n* or 501-2 to 501-*n* and the electronic device 1001 based on similarity between the received body information and the prior body information stored in each of the at least one external electronic device 401-2 to 401-*n* or 501-2 to 501-*n* and the electronic device 1001. Here, the prior body information may be body information finally stored in each corresponding device.

For example, the processor 1040 may calculate a distance-based similarity between the received body information and the prior body information stored in the electronic device 1001. The processor 1040 may receive the distance-based similarity between the received body information and the prior body information stored in each external electronic device from the at least one external electronic device 401-2 to 401-*n* or 501-2 to 501-*n*. For example, the at least one external electronic device 401-2 to 401-*n* or 501-2 to 501-*n* may calculate the distance-based similarity between the body information received from the electronic device 1001 and the prior body information stored in the corresponding external electronic device and transmit the similarity to the electronic device 1001. In other words, the processor 1040 may receive the distance-based similarity calculated by each corresponding external electronic device from each of the at least one external electronic device 401-2 to 401-*n* or 501-2 to 501-*n*. In this disclosure, the distance-based similarity may be an Euclidean distance-based similarity in body information.

The Euclidean distance-based similarity may be calculated based on Equation 1 above. The similarities individually calculated by the electronic device 1001 and the at least one external electronic device 401-2 to 401-*n* or 501-2 to 501-*n* using Equation 1 are assumed to be the same as those shown in Table 1 above.

The processor 1040 may compare the similarity calculated by the electronic device 1001 with the similarities of the external electronic devices 401-2 to 401-*n* or 501-2 to 501-*n*. For example, the processor 1040 may receive the similarity calculated by each of the at least one external electronic device 401-2 to 401-*n* or 501-2 to 501-*n*. The similarities calculated by the electronic device 1001 and the similarities received from the at least one external electronic device 401-2 to 401-*n* or 501-2 to 501-*n* are assumed to be the same as those shown in Table 1 above.

The processor 1040 may determine that the device having the minimum value of the similarity of the at least one external electronic device 401-2 to 401-*n* or 501-2 to 501-*n* and the similarity calculated by the electronic device 1001 corresponds to the received body information.

For example, it may be known from Table 1 that, among the electronic device 1001 and the at least one external electronic device 401-2 to 401-*n* or 501-2 to 501-*n*, the second external electronic device 401-2 or 501-2 has the minimum similarity. In this case, the processor 1040 may determine that the device (e.g., the second external electronic device 401-2 or 501-2) of the minimum similarity is a device corresponding to the body information received from the external body information obtaining device 400.

The processor 1040 may perform control to store the received body information in the device determined to correspond to the received body information and to delete the received body information from the other devices. For example, the processor 1040 may transmit a command for storing the received body information to the determined device and commands for deleting the received body information to the other devices.

According to an embodiment of the present disclosure, where the minimum similarity is the similarity calculated by the electronic device 1001, the processor 1040 may determine that the electronic device 1001 corresponds to the received body information, and the processor 1040 may store the received body information in the memory 1020 of the electronic device 1001. For example, the processor 1040 may generate a command for storing the received body information and deliver the command to the memory 1020.

The processor 1040 may load the information related to the at least one external electronic device 401-2 to 401-*n* or 501-2 to 501-*n* in the group 425 or 525 (WS1) from the memory 1020 and generate a command for deleting the received body information corresponding to each of the at least one external electronic device 401-2 to 401-*n* or 501-2 to 501-*n* based on the information. The processor 1040 may transmit the generated command for deleting the received body information to each of the at least one external electronic device 401-2 to 401-*n* or 501-2 to 501-*n*.

The processor 1040 may transmit the command for deleting the received body information to each external electronic device using, e.g., the network address information of the external electronic device among the pieces of information loaded. The processor 1040 may establish a communication link with each corresponding external electronic device using the ID number of the external electronic device among the pieces of loaded information and transmit the command for deleting the received body information corresponding to the external electronic device to the external electronic device for which a communication link has been established.

According to an embodiment of the present disclosure, when the minimum similarity is the similarity of one (e.g., the second external electronic device 401-2 or 501-2) among the at least one external electronic device 401-2 to 401-*n* or 501-2 to 501-*n* in the group 425 or 525 (WS1), the processor 1040 may determine that the second external electronic device 401-2 or 501-2 corresponds to the received body information, and the processor 1040 may delete the received body information from the memory 1020 of the electronic device 1001. For example, the processor 1040 may generate a command for deleting the received body information and deliver the command to the memory 1020.

The processor 1040 may load the information related to the second external electronic device 401-2 or 501-2 in the group 425 or 525 from the memory 1020 and generate a command for storing the received body information based on the information related to the second external electronic device 401-2 or 501-2. The processor 1040 may transmit the command for storing the received body information, generated based on the information related to the second external electronic device 401-2 or 501-2, to the second external electronic device 401-2 or 501-2. For example, the processor 1040 may transmit the command for storing the received body information, generated corresponding to the second external electronic device 401-2 or 501-2, to the second external electronic device 401-2 or 501-2 using the network address information of the second external electronic device 401-2 or 501-2. The processor 1040 may establish a communication link with the second external electronic device 401-2 or 501-2 using the ID number of the second external electronic device 401-2 or 501-2 and transmit the command for storing the received body information, generated corresponding to the second external electronic device 401-2 or 501-2, to the second external electronic device 401-2 or 501-2 for which a communication link has been established. The processor 1040 may transmit a command for deleting the received body information to each of the other external electronic devices 401-3 to 401-*n* or 501-3 to 501-*n* than the second external electronic device 401-2 or 501-2 among the at least one external electronic device 401-2 to 401-*n* or 501-2 to 501-*n*. For example, the processor 1040 may generate a command for deleting the received body information corresponding to each of the other external electronic devices 401-3 to 401-*n* or 501-3 to 501-*n* among the at least one external electronic device 401-2 to 401-*n* or 501-2 to 501-*n* based on the registration information of the at least one external electronic device 401-2 to 401-*n* or 501-2 to 501-*n* in the group 425 or 525 (WS1) from the memory 1020. The processor 1040 may transmit the command for deleting the received body information, generated corresponding to each of the other external electronic devices 401-3 to 401-*n* or 501-3 to 501-*n*, to each of the other external electronic devices 401-3 to 401-*n* or 501-3 to 501-*n* using the network address information of the other external electronic devices 401-3 to 401-*n* or 501-3 to 501-*n*. The processor 1040 may establish a communication link with each of the other external electronic devices 401-3 to 401-*n* or 501-3 to 501-*n* using the ID number of each of the other external electronic devices 401-3 to 401-*n* or 501-3 to 501-*n* and transmit the command for deleting the received body information, generated corresponding to each of the other external electronic devices 401-3 to 401-*n* or 501-3 to 501-*n*, to each of the other external electronic devices 401-3 to 401-*n* or 501-3 to 501-*n* which has established the communication link.

According to an embodiment of the present disclosure, an electronic device 1001 may include a communication circuit 1010 wirelessly communicating with an external electronic device, a memory 1020 storing body information, and a processor 1040 configured to transmit the body information received from an external body information obtaining device (e.g., the body information obtaining device 400 or 500) to a server (e.g., the server 606), receive a command for the received body information from the server 606, and process the received body information based on the received command.

According to an embodiment of the present disclosure, the processor 1040 may be configured to, upon receiving a command for storing the received body information from the server 606, store the received body information in the memory 1020.

According to an embodiment of the present disclosure, the processor 1040 may be configured to, upon receiving a command for deleting the received body information from the server 606, delete the received body information.

According to an embodiment of the present disclosure, the processor 1040 may be configured to send a request for information related to at least one external electronic device in a group related to the external body information obtaining device 400 or 500 to the server 606, to receive the information related to the at least one external electronic device in the group in response to the request, to transmit the received body information to the at least one external electronic device based on the received information related to the at least one external electronic device, to determine a device corresponding to the received body information among the at least one external electronic device and the electronic device based on the received body information and prior body information stored in each of the at least one external electronic device and the electronic device, and to transmit the received body information to the determined device.

According to an embodiment of the present disclosure, the processor 1040 may be configured to determine the device corresponding to the received body information among the at least one external electronic device 401-2 to 401-*n* or 501-2 to 501-*n* and the electronic device 1001 based on a similarity between the received body information and the prior body information stored in each of the at least one external electronic device 401-2 to 401-*n* or 501-2 to 501-*n* and the electronic device 1001.

According to an embodiment of the present disclosure, the processor 1040 may be configured to calculate a distance-based similarity between the received body information and the prior body information of the electronic device 1001, to receive a distance-based similarity between the received body information and the prior body information of each of the at least one external electronic device 401-2 to 401-*n* or 501-2 to 501-*n* from the at least one external electronic device, and to compare the calculated distance-based similarity and the received distance-based similarity to determine that a device having a minimum similarity corresponds to the received body information.

According to an embodiment of the present disclosure, the distance-based similarity may be an Euclidean distance-based similarity.

According to an embodiment of the present disclosure, the processor 1040 may be configured to store the received body information in the memory 1020 and transmit a command for deleting the received body information to the at least one external electronic device 401-2 to 401-*n* or 501-2 to 501-*n* when the determined device is the electronic device 1001.

According to an embodiment of the present disclosure, when the determined device is one of the at least one external electronic device 401-2 to 401-*n* or 501-2 to 501-*n*, the processor 1040 may be configured to delete the received body information from the memory 1020 and transmit a command for storing the received body information to the one of the at least one external electronic device and a command for deleting the received body information to the other external electronic device.

According to an embodiment of the present disclosure, the processor 1040 may be configured to store, in the memory 1020, a group (e.g., the group 425 or 525) including information related to the at least one external electronic device and the electronic device 1001.

According to an embodiment of the present disclosure, the processor 1040 may be configured to transmit the received body information to a corresponding external electronic device based on network address information of each of the at least one external electronic device in the group stored in the memory 1020 when the group 425 or 525 is registered in the electronic device 1001.

Figure 11:
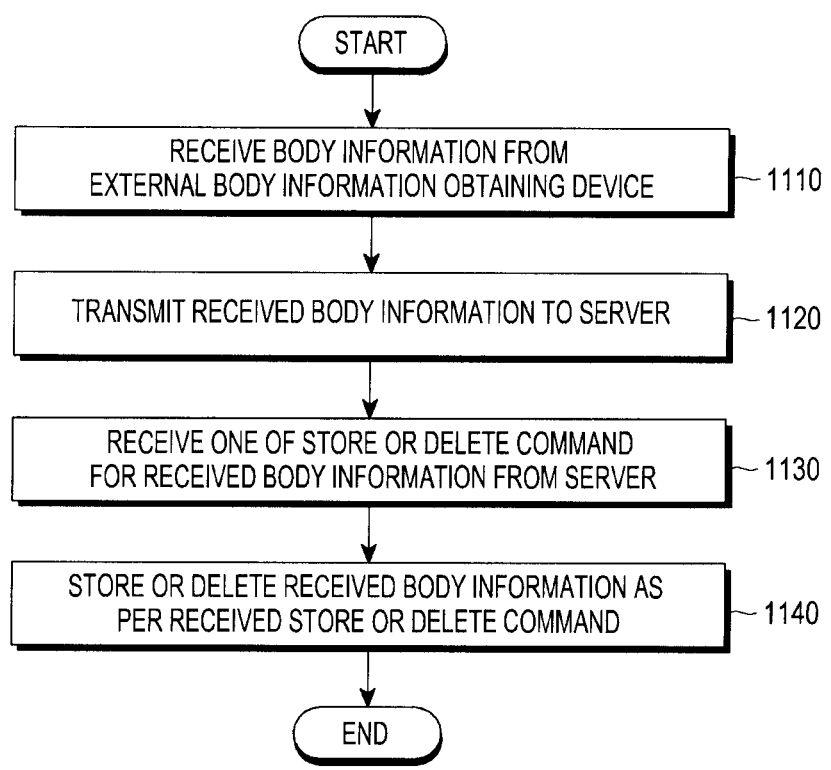
FIG. 11 is a block diagram illustrating a method for managing body information by an electronic device according to an embodiment of the present disclosure.

FIG. 11 is a flowchart illustrating a method for managing body information by an electronic device according to an embodiment of the present disclosure. The body information managing method may be performed by at least one of an electronic device (e.g., the electronic device 1001) or a processor 1040 of the electronic device.

In operation 1110, the electronic device may receive body information obtained by an external body information obtaining device (e.g., the external body information obtaining device 400 or 500) from the external body information obtaining device.

For example, the electronic device may establish a wireless communication link when the electronic device is positioned within a short-range communicable range from the external body information obtaining device. Where the electronic device is an electronic device having finally established a communication link with the external body information obtaining device, the electronic device may receive the body information obtained by the external body information obtaining device from the external body information obtaining device through the communication circuit (e.g., the communication circuit 1010).

In operation 1120, the electronic device, upon receiving the body information from the external body information obtaining device, may transmit the received body information to a server (e.g., the server 606).

According to an embodiment of the present disclosure, the received body information may include at least one of, e.g., the user's height, weight, body fat, bone mineral density, skeletal muscle mass, muscle strength, body water level, body fat (e.g., body mass index), basal metabolic rate, biological information, or a combination thereof. The biological information may include, e.g., a biological signal, such as, e.g., an electrocardiography (ECG) signal, an electroencephalogram (EEG) signal, an electrooculogram (EOG) signal, an electrogastrogram (EGG) signal, or an electromyography (EMG) signal, a heart rate, a cardiac cycle, a cardiac cycle standard deviation, a pulse rate, arrhythmia, blood volume impedance, or a stress level. The body information is not limited thereto, and the body information may also include various body-related measurements.

In operation 1130, the electronic device may receive one of a command for deleting the received body information or a command for storing the received body information from the server. For example, in response to the transmission of the received body information from the server according to the determination of the server, the electronic device may receive the command for storing the received body information in the memory (e.g., the memory 1020) of the electronic device. In response to the transmission of the received body information from the server according to the determination of the server, the electronic device may receive a command for deleting the received body information from the memory of the electronic device.

In operation 1140, the electronic device may store or delete the received body information according to the store command or delete command received from the server.

For example, upon receiving the command for storing the received body information from the server, the electronic device may store the received body information in the memory. For example, the electronic device may cumulatively store the received body information in the memory or update the prior body information which used to be stored in the electronic device with the received body information. Upon receiving the command for deleting the received body information from the server, the electronic device may delete the received body information from the memory.

Figure 12:
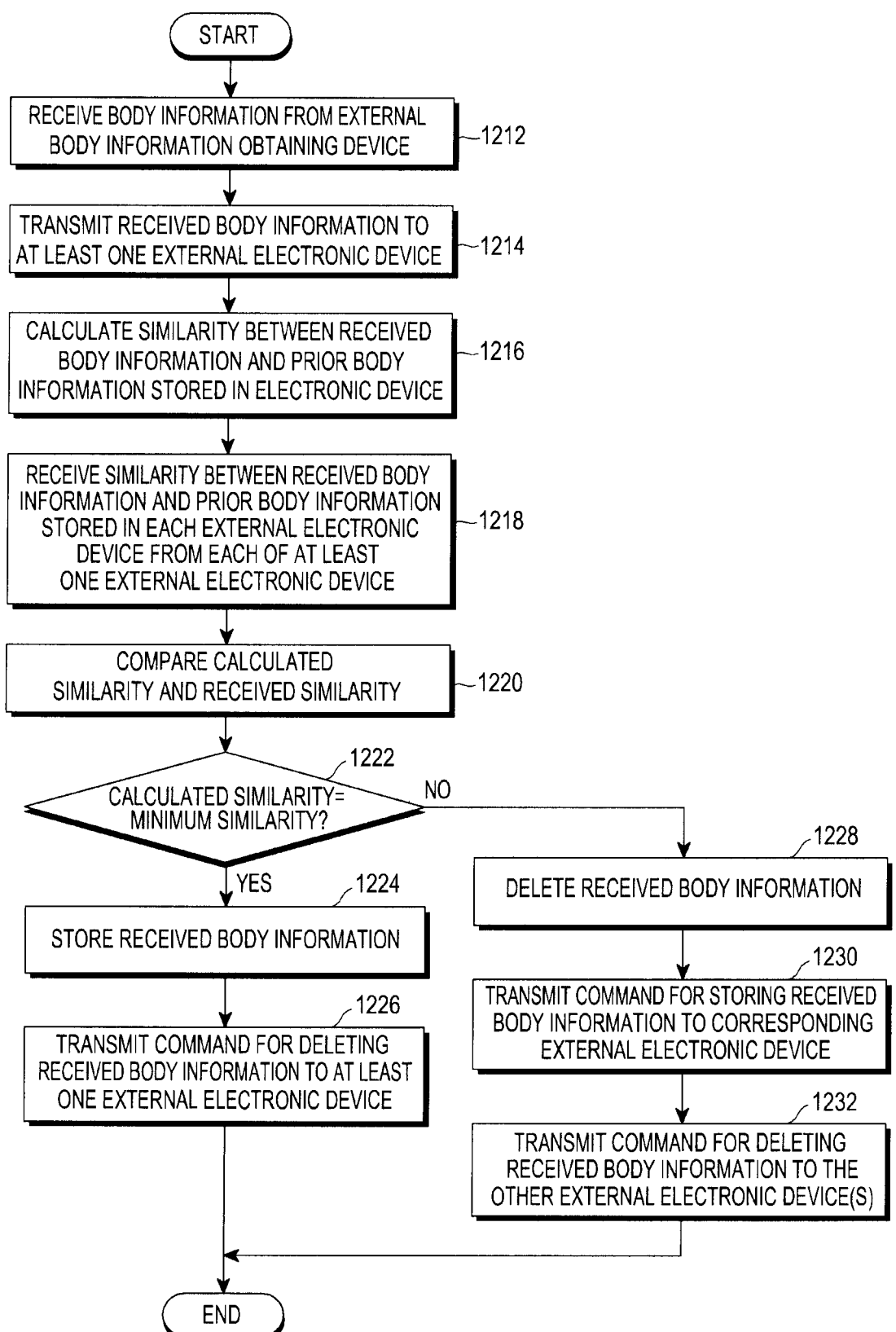
FIG. 12 is a block diagram illustrating a method for managing body information by an electronic device according to an embodiment of the present disclosure.

FIG. 12 is a flowchart illustrating a method for managing body information by an electronic device according to an embodiment of the present disclosure. The body information managing method may be performed by at least one of an electronic device (e.g., the electronic device 1001) or a processor 1040 of the electronic device.

In operation 1212, the electronic device may receive body information from an external body information obtaining device (e.g., the body information obtaining device 400 or 500). Operation 1310 is the same as operation 1210 of FIG. 12, and thus, the description of operation 1210 may apply to operation 1310.

In operation 1214, the electronic device may transmit the received body information to at least one external electronic device.

For example, upon receiving the body information obtained by and transmitted from the external body information obtaining device, the electronic device may transmit a request to a server for information related to at least one external electronic device (e.g., the at least one external electronic device 401-2 to 401-n or 501-2 to 501-n) in a predefined group and receive the information from the server in response.

According to an embodiment of the present disclosure, the information related to the at least one external electronic device in the group may include network address information.

According to an embodiment of the present disclosure, where the server is not provided, the memory (e.g., the memory 1020) of the electronic device may store a group (e.g., the group 425 or 525) including the information related to the at least one external electronic device related to the external body information obtaining device stored in the server. For example, the electronic device may receive a request for the group 425 or 525 including the information related to the corresponding electronic device from the at least one external electronic device related to the external body information obtaining device and store in the memory. The information related to the external electronic device may include at least one of, e.g., information (e.g., device ID) for identifying the external electronic device, information (e.g., group ID such as "WS1") for identifying the group (e.g., group 403) where the external electronic device belongs, network address information (e.g., MAC address) of the external electronic device, body information about the user of the external electronic device, information (e.g., device ID) for identifying a body information obtaining device related to the external electronic device, or a combination thereof.

The electronic device may transmit the body information to the at least one external electronic device included in the group related to the external body information obtaining device. For example, the electronic device may transmit the received body information to the at least one external electronic device using the network address information among pieces of information related to the at least one external electronic device in the group.

In operation 1216, the electronic device may calculate a similarity between the received body information and the prior body information stored in the electronic device. For example, the electronic device may calculate a distance-based similarity between the received body information and the prior body information stored in the memory of the electronic device.

In operation 1218, the electronic device may receive a number of similarities between the received body information and the prior body information stored for each of the one or more external electronic devices, transmitted from each of the one or more external electronic devices. For example, each of the one or more external electronic device included in the group stored in the electronic device may calculate the distance-based similarity between the received body information and its prior body information and transmit the distance-based similarity to the electronic device. In other words, the electronic device may receive distance-based similarities calculated by each of the one or more external electronic devices.

According to an embodiment of the present disclosure, the distance-based similarity used in operations 1316 and 1318 may be, e.g., an Euclidean distance-based body information similarity.

In operation 1220, the electronic device may compare the similarity calculated by the electronic device and the similarities received from each of the one or more external electronic devices and determine which of the received similarities indicates a minimum similarity.

In operation 1222, the electronic device may determine whether the minimum similarity was the similarity calculated by the electronic device. In operation 1222, when the minimum similarity was the similarity calculated by the electronic device, operation 1224 is performed, and operation 1228 is otherwise performed.

In operation 1224, when the minimum similarity was calculated by the electronic device, the electronic device may store the received body information. For example, when the minimum similarity was calculated by the electronic device, the electronic device may determine that the electronic device corresponds to the received body information, and thus cumulatively store the received body information in the memory of the electronic device, or update the prior body information previously stored in the electronic device with the received body information.

In operation 1226, the electronic device may transmit a command to delete the received body information to each of the one or more external electronic devices. For example, the electronic device may generate a command for deleting the received body information corresponding for each of the one or more external electronic devices based on the information related to each of the at least one external electronic device in the group stored in the memory. The electronic device may transmit the command to each external electronic device. The electronic device may transmit the command using, for example, the network address information of the external electronic device. The electronic device may establish a communication link with each corresponding external electronic device using the ID number of the external electronic device for transmission of the command for deletion.

In operation 1228, when the minimum similarity does not match the similarity calculated by the electronic device, the electronic device may delete the received body information. For example, when the minimum similarity is not the similarity calculated by the electronic device, the electronic device may determine that one of the one or more external electronic devices corresponds to the received body information. In other words, the electronic device may determine that the electronic device does not correspond to the received body information, and delete the received body information from the memory of the electronic device in response. For example, the electronic device may generate a command for deleting the received body information and transmit the command to memory.

In operation 1230, the electronic device may transmit a command for storing the received body information to the external electronic device (e.g., the external electronic device 401-2 or 501-2) corresponding to the minimum similarity among the at least one external electronic device. For example, the electronic device may determine that the second external electronic device corresponding to the similarity among the at least one external electronic device corresponds to the received body information. The electronic device may generate a command for storing the received body information corresponding to the second external electronic device based on the information related to the at least one external electronic device in the group stored in the memory. The electronic device may transmit the command for storing the received body information, generated based on the information related to the second external electronic device, to the determined external electronic device (e.g., the second external electronic device). For example, the electronic device may transmit, to the determined external electronic device (e.g., the second external electronic device), the command for storing the received body information generated corresponding to the determined external electronic device using the network address information (e.g., EE:FF:GG:HH) of the determined external electronic device (e.g., the second external electronic device). The electronic device may establish a communication link with the determined external electronic device (e.g., the second external electronic device) using the ID information of the determined external electronic device (e.g., the second external electronic device) and transmit, to the determined external electronic device (e.g., the second external electronic device) that has established the communication link, the command for storing the received body information generated corresponding to the determined external electronic device.

In operation 1232, the electronic device may transmit a command for deleting the received body information to each of the other external electronic devices 401-3 to 401-*n* or 501-3 to 501-*n* than the determined external electronic device (e.g., the second external electronic device) among the at least one external electronic device. For example, the electronic device may generate a command for deleting the received body information corresponding to each of the other external electronic devices of the at least one external electronic device based on the information related to each of the at least one external electronic device in the group stored in the memory. The electronic device may transmit the command for deleting the received body information generated corresponding to each of the other external electronic devices to each of the other external electronic devices using the network address information of each of the other external electronic devices. The electronic device may establish a communication link with each of the other external electronic devices using the ID number of each of the other external electronic devices and transmit the command for deleting the received body information generated corresponding to each of the other external electronic devices to each of the other external electronic devices.

Figure 13:
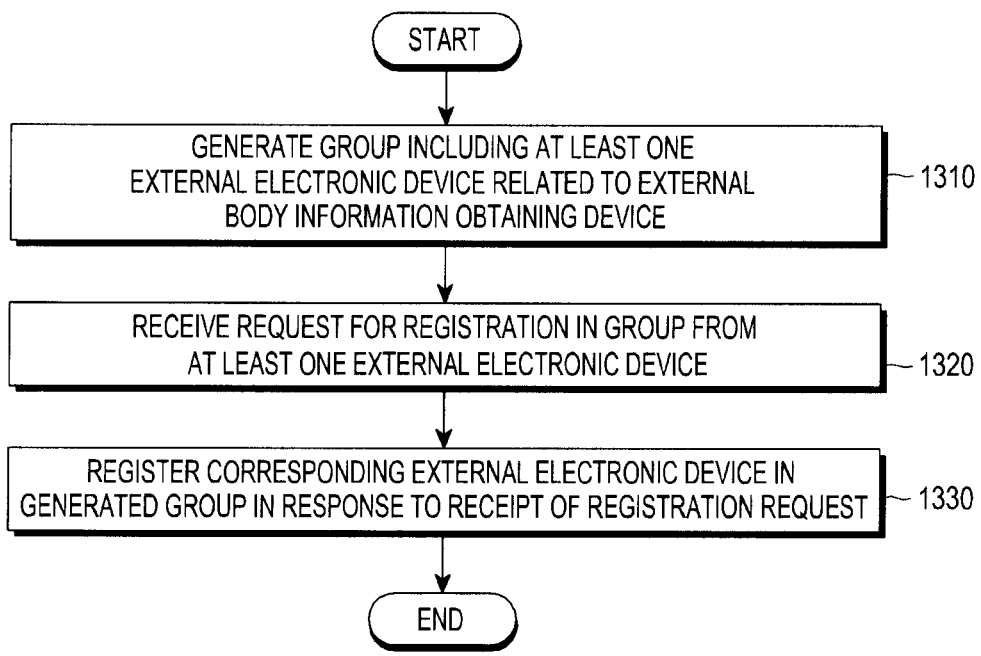
FIG. 13 is a block diagram illustrating a method for managing body information by an electronic device according to an embodiment of the present disclosure.

FIG. 13 is a flowchart illustrating a method for managing body information by an electronic device according to an embodiment of the present disclosure. The body information managing method shown in FIG. 13 illustrates a method for registering at least one external electronic device related to an external body information obtaining device (e.g., in the group 425 or 525 stored in the electronic device). The method may be performed by at least one of an electronic device (e.g., the electronic device 1001) or a local processor (e.g., the processor 1040) of the electronic device.

In operation 1310, the electronic device may generate a group (e.g., the group 425 or 525 "WS1") including at least one external electronic device (e.g., the external electronic device 401-2 to 401-*n* or 501-2 to 501-*n*) related to the external body information obtaining device (e.g., the external body information obtaining device 400 or 500). For example, the electronic device may generate the group including the electronic device related to the external body information obtaining device and the at least one external electronic device in the group managing database 1025 of the memory (e.g., the memory 1020) of the electronic device.

In operation 1320, the electronic device may receive a request from at least one external electronic device to register with the group. For example, the electronic device may receive a registration request message from the at least one external electronic device related to the external body information obtaining device. The request may include information related to the at least one external electronic device, including for example information (e.g., device ID) identifying the external electronic device, information (e.g., group ID such as WS1) identifying the group to which the external electronic device belongs, network address information (e.g., MAC address) of the external electronic device, body information about the user of the external electronic device, information (e.g., device ID) identifying the external body information obtaining device related to the external electronic device, or a combination thereof.

In operation 1330, the electronic device may register the external electronic device in the generated group in response to the registration request. For example, the electronic device may obtain the information related to the at least one external electronic device from the registration request message in response to the request for registration in the group from the at least one external electronic device. The electronic device may store the obtained information in the group generated in the memory of the electronic device to update the information. For example, in the group related to the external body information obtaining device, the information related to the at least one external electronic device may be stored in the form of a lookup table in the group managing database inside the memory of the electronic device.

When the registration of the device in the group is complete in response to the registration request, the electronic device may transmit a registration response message indicating that the corresponding electronic device has been registered in the group to the external electronic device.

Figure 14:
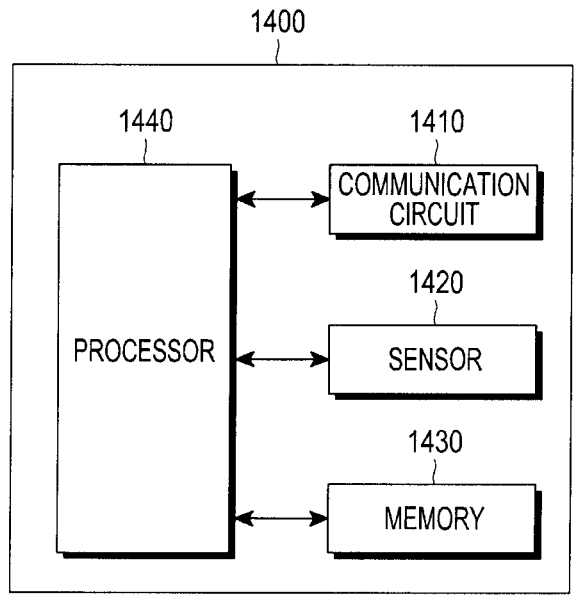
FIG. 14 is a block diagram illustrating a body information obtaining device according to an embodiment of the present disclosure.

FIG. 14 is a block diagram illustrating a body information obtaining device according to an embodiment of the present disclosure.

Referring to FIG. 14, according to an embodiment of the present disclosure, a body information obtaining device 1400 may include at least one of a communication circuit 1410, a sensor 1420, a memory 1430, or a processor 1440. FIG. 14 illustrates components related to embodiments of the present disclosure, and other components than the above-listed components may also be included. For example, the body information obtaining device 1400 of FIG. 14 may include the whole or part of the electronic device 101 of FIG. 1, the electronic device 201 of FIG. 2, the body information obtaining device 400 of FIGS. 4a to 4d, or the body information obtaining device 500 of FIGS. 5a to 5d.

The communication circuit 1410 may establish a communication link or connection with at least one external electronic device (e.g., the electronic devices 401-1 to 401-n of FIGS. 4a to 4d or the electronic devices 501-1 to 501-n of FIGS. 5a to 5d).

The communication circuit 1410 may include the whole or part of, e.g., the communication interface 170 of FIG. 1 or the communication module 220 of FIG. 2. The communication circuit 1410 may also be termed a communication unit or communication module, or may include a communication unit or communication module as part thereof, or may configure a communication unit or communication module.

According to an embodiment of the present disclosure, the communication circuit 1410 may provide data based on short-range communication. For example, the communication circuit 1410 may establish a communication link with at least one external electronic device (e.g., the electronic devices 401-1 to 401-n or 501-1 to 501-n) connected with a short-range communication-based network. For example, the communication circuit 1410 may include at least one of, e.g., a wireless fidelity (Wi-Fi), BlueTooth, near-field communication (NFC), zigbee, z-wave, or global navigation satellite system (GNSS) module or unit.

Upon establishing a communication link with the at least one external electronic device 401-2 to 401-n or 501-2 to 501-n, the communication circuit 1410 may transmit the body information detected through the sensor 1420 of the body information obtaining device 1400 or stored in the memory 1430 to the external electronic device finally connected for communication (e.g., the first electronic device 401-1 or 501-1).

The sensor 1420 may include at least one sensor capable of detecting the user's body information. For example, the sensor 1420 may include at least one of a weight sensor capable of detecting the user's weight, a body composition sensor capable of measuring the body composition, or a biological signal measuring sensor capable of measuring a biological signal. The at least one sensor, however, is not limited thereto, and any other sensor may also be included which is able to detect the user's body information.

The memory 1430 may store commands or data related to at least one other component of the body information obtaining device 1400. The memory 1430 may include the whole or part of the memory 130 of FIG. 1 or the memory 230 of FIG. 2. The memory 1430 may store the body information detected through the sensor 1420. The memory 1430 may cumulatively store different pieces of body information that are obtained several times.

The processor 1440 may overall control the body information obtaining device 1400. For example, the processor 1440 may perform control to detect the user's body information through the sensor 1420. According to an embodiment of the present disclosure, the detected body information may include not only the user's height, weight, impedance, skin conductivity, or other body information directly detected through the sensor 1420 but also the results of body composition analysis, such as the body fat, bone mineral density, skeletal muscle mass, muscle strength, body water level, body mass (BMI), or basal metabolic rate which have been analyzed based on the detected body information. The detected body information may include, e.g., a biological signal, such as, e.g., an electrocardiography (ECG) signal, an electroencephalogram (EEG) signal, an electrooculogram (EOG) signal, an electrogastrogram (EGG) signal, or an electromyography (EMG) signal, a heart rate, a cardiac cycle, a cardiac cycle standard deviation, a pulse rate, arrhythmia, blood volume impedance, or a stress level.

The processor 1440 may transmit the detected body information to the external electronic device (e.g., the first electronic device 401-1) finally connected to the body information obtaining device 1400 for communication among the at least one external electronic device 401-2 to 401-n or 501-2 to 501-n in the group 425 or 525. When failing to establish a communication link with one of the at least one external electronic device after the body information has been detected, the processor 1440 may cumulatively store the detected body information until one of the at least one external electronic device forms a communication link with the body information obtaining device 1400. Thereafter, when one (e.g., 401-1 or 501-1) of the at least one external electronic device 401-2 to 401-$n$ or 501-2 to 501-$n$ is connected to the body information obtaining device 1400 for communication, the processor 1440 may transmit the accrued body information to the external electronic device 401-1 or 501-1 connected for communication.

Figure 15:
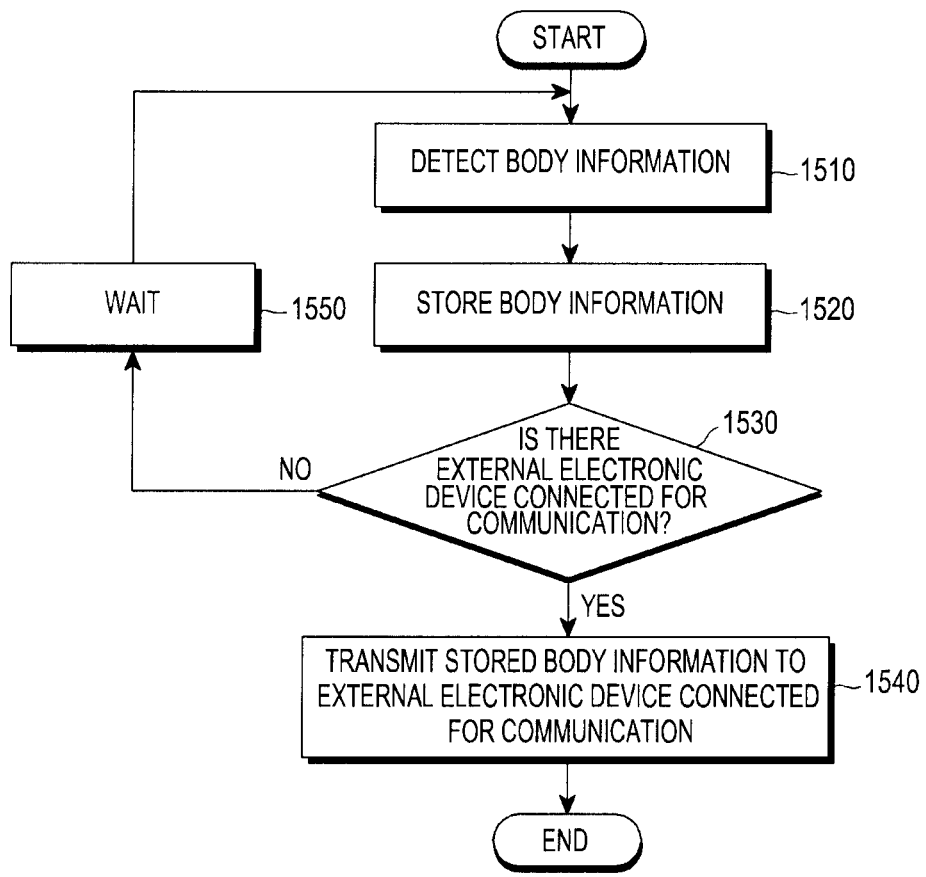
FIG. 15 is a flowchart illustrating a method for managing body information by a body information obtaining device according to an embodiment of the present disclosure.

FIG. 15 is a flowchart illustrating a method for managing body information by a body information obtaining device according to an embodiment of the present disclosure. The body information managing method may be performed by one of a body information obtaining device (e.g., the body information obtaining device 1400) or a processor (e.g., the processor 1440) of the electronic device.

In operation 1510, the body information obtaining device may detect the user's body information through a sensor (e.g., the sensor 1420). For example, the body information may include at least one of, for example, the user's height, weight, body fat, bone mineral density, skeletal muscle mass, muscle strength, body water level, body fat (e.g., body mass index), basal metabolic rate, biological information, or a combination thereof. The biological information may include, e.g., a biological signal, such as, e.g., an electrocardiography (ECG) signal, an electroencephalogram (EEG) signal, an electrooculogram (EOG) signal, an electrogastrogram (EGG) signal, or an electromyography (EMG) signal, a heart rate, a cardiac cycle, a cardiac cycle standard deviation, a pulse rate, arrhythmia, blood volume impedance, or a stress level. The body information is not limited thereto, and the body information may also include various body-related measurements.

In operation 1520, the body information obtaining device may store the detected body information in the memory of the body information obtaining device.

In operation 1530, the body information obtaining device may determine whether there is an external electronic device connected with the body information obtaining device for communication. In operation 1530, the body information obtaining device may detect whether there is an external electronic device communicatively connected with the body information obtaining device. In operation 1550, when there is no external electronic device communicatively coupled with the body information obtaining device, the device may wait a predetermined time period before returning to operation 1510 (as described further below).

In operation 1540, when there is an external electronic device connected with the body information obtaining device for communication, the body information obtaining device may transmit the stored body information to the external electronic device through the communication circuit.

In operation 1530, when there is no external electronic device connected with the body information obtaining device for communication, the body information obtaining device may perform operation 1550.

In operation 1550, when there is no external electronic device connected with the body information obtaining device for communication, the body information obtaining device may wait to obtain or detect other body information. For example, upon detecting other body information after waiting to detect other body information, the body information obtaining device may perform operation 1510 to periodically or non-periodically repeat the subsequent operations.

For example, when there is no external electronic device connected with the body information obtaining device for communication while different pieces of body information are detected multiple times as operations 1510 to 1530 repeat, the detected pieces of body information may cumulatively be stored in operation 1520. Such operations may be repeated until an external electronic device is connected to the body information obtaining device for communication. When an external electronic device is connected with the body information obtaining device for communication (operation 1530) after the body information is detected multiple times and cumulatively stored in the memory of the body information obtaining device, the body information obtaining device may transmit all of the pieces of body information cumulatively stored to the external electronic device connected for communication in operation 1540.

Figure 16:
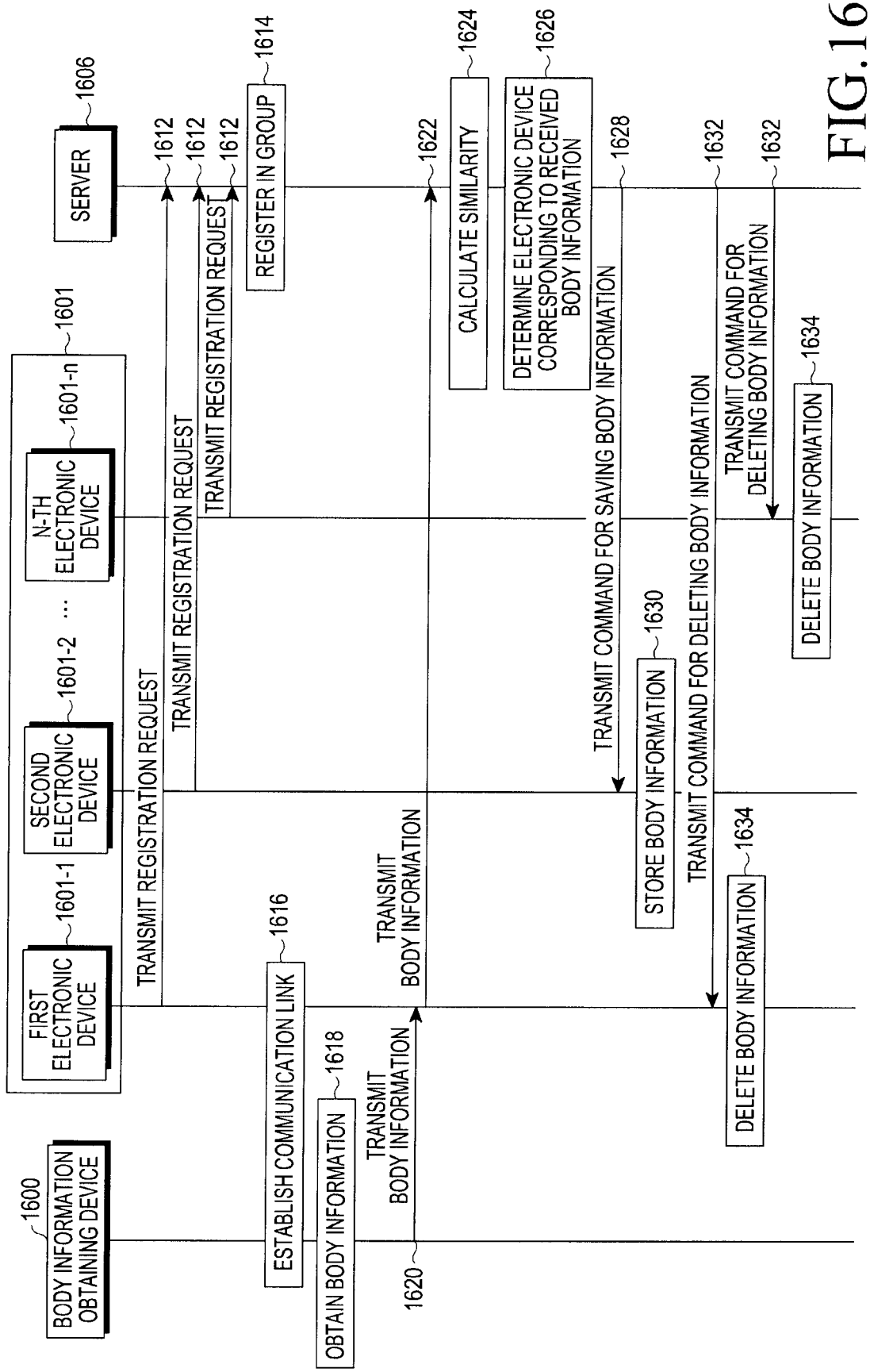
FIG. 16 is a flowchart illustrating a method for managing body information according to an embodiment of the present disclosure.

FIG. 16 is a flowchart illustrating a method for managing body information according to an embodiment of the present disclosure. FIG. 16 illustrates components related to embodiments of the present disclosure, and other components than the above-listed components may also be included. Referring to FIG. 16, a first electronic device 1601-1 of a plurality of electronic devices 1601-1 to 1601-$n$ is assumed to finally be connected to a body information obtaining device 1600 for communication, and an electronic device corresponding to body information (e.g., the body information 400$a$ or 500$a$) obtained by the body information obtaining device 1600 is assumed to a second electronic device 1601-2.

In operation 1612, each of at least one electronic device 1601-1 to 1601-$n$ sharing the body information obtaining device 1600 may transmit a registration request message requesting registration in a group (e.g., the group 403) including the at least one electronic device 1601-1 to 1601-$n$ to the server 1606.

In operation 1614, the server 1606 may receive respective registration information related to each electronic device from the registration request messages and store all received information for the group 403, registering electronic devices 1601-1 to 1601-$n$ in the group 403. When any electronic device is registered in the group 403, the server 1606 may transmit a response message confirming that the corresponding electronic device has been registered in the group 403 for the corresponding electronic device.

In operation 1616, the body information obtaining device 1600 and one of the at least one electronic device in the group (e.g., the first electronic device 1601-2) may establish a short-range communication link. The electronic device (e.g., the first electronic device 1601-2) may communicatively connect with the body information obtaining device 1600 while disposed within a short-range communication range from the body information obtaining device 1600.

In operation 1618, the body information obtaining device 1600 may obtain the user's body information (e.g., the body information 400$a$ or 500$a$). According to an embodiment of the present disclosure, the body information may be obtained prior operation 1616. For example, the different pieces of body information may be obtained by the body information obtaining device 1600 prior to the body information obtaining device 1600 establishing a communication link with one of the at least one electronic device 1601-1 to 1601-$n$ in the group 403, and may thus already have been cumulatively be stored in the memory (e.g., the memory 1430) of the body information obtaining device 1600.

In operation 1620, the body information obtaining device may transmit the obtained body information to the electronic device (e.g., the first electronic device 1601-1) communicative coupled with the body information obtaining device 1600. According to an embodiment of the present disclosure, the body information obtaining device 1600 may simultaneously transmit all body information accrued in the memory 1430 to the electronic device (e.g., the first electronic device 1601-1) communicatively coupled with the body information obtaining device 1600 for communication.

In operation 1622, upon receiving the body information 400*a* or 500*a* obtained by the body information obtaining device 1600, the electronic device (e.g., the first electronic device 1601-1) may transmit the received body information 400*a* or 500*a* to the server 1606.

In operation 1624, the server 1606 may calculate a similarity between the received body information 400*a* or 500*a* and body information stored for each electronic device 1601-1 to 1601-*n* in the group 403. According to an embodiment of the present disclosure, the similarity may be an Euclidean distance-based similarity.

In operation 1626, the server 1606 may compare the calculated similarities and determine that the electronic device corresponding to the minimum similarity of the at least one electronic device 1601-1 to 1601-*n* in the group 403 is the device (e.g., the second electronic device 1601-2) corresponding to the received body information 400*a* or 500*a*.

In operation 1628, the server 1606 may transmit a signal including a command for storing the received body information 400*a* or 500*a* to the electronic device (e.g., the second electronic device 1601-2) determined to correspond to the received body information 400*a* or 500*a* (which, in this example is the second electronic device 1601-2).

In operation 1630, the electronic device (e.g., the second electronic device 1601-2) determined to correspond to the received body information 400*a* or 500*a* may store the received body information 400*a* or 500*a* in the memory of the electronic device (e.g., the second electronic device 1601-2) according to the command for storing the received body information 400*a* or 500*a* received from the server 1606. According to an embodiment of the present disclosure, the received body information 400*a* or 500*b* may cumulatively be stored in the memory, or the body information previously stored in the memory may be updated with the received body information 400*a* or 500*a*.

In operation 1632, the server 1606 may transmit a signal including a command for deleting the received body information 400*a* or 500*a* to each of the other electronic devices (e.g., the first electronic device 1601-1 and the n-th electronic device 1601-*n*) in the group 403 than the electronic device (e.g., the second electronic device 1601-2) determined to correspond to the received body information 400*a* or 500*a*.

In operation 1634, each of the other electronic devices (e.g., the first electronic device 1601-1 and the n-th electronic device 1601-*n*) may delete the received body information 400*a* or 500*a* responsive to the command for deleting the received body information 400*a* or 500*a* received from the server 1606. According to an embodiment of the present disclosure, the body information 400*a* or 500*a* temporarily stored in each of the other electronic devices (e.g., the first electronic device 1601-1 and the n-th electronic device 1601-*n*) may be not saved in the memory of the electronic device but deleted.

The term 'module' may refer to a unit including one of hardware, software, and firmware, or a combination thereof. The term 'module' may be interchangeably used with a unit, logic, logical block, component, or circuit. The module may be a minimum unit or part of an integrated component. The module may be a minimum unit or part of performing one or more functions. The module may be implemented mechanically or electronically. For example, the module may include at least one of Application Specific Integrated Circuit (ASIC) chips, Field Programmable Gate Arrays (FPGAs), or Programmable Logic Arrays (PLAs) that perform some operations, which have already been known or will be developed in the future.

At least a part of the device (e.g., modules or their functions) or method (e.g., operations) may be implemented as instructions stored in a computer-readable storage medium e.g., in the form of a programming module. The instructions, when executed by a processor (e.g., the processor 120), may enable the processor to carry out a corresponding function. The computer-readable storage medium may be e.g., the memory 130.

The computer-readable storage medium may include a hardware device, such as hard discs, floppy discs, and magnetic tapes (e.g., a magnetic tape), optical media such as compact disc ROMs (CD-ROMs) and digital versatile discs (DVDs), magneto-optical media such as floptical disks, ROMs, RAMs, flash memories, and/or the like. Examples of the program commands may include not only machine language codes but also high-level language codes which are executable by various computing means using an interpreter. The aforementioned hardware devices may be configured to operate as one or more software modules to carry out example embodiments of the present disclosure, and vice versa.

Modules or programming modules in accordance with various embodiments of the present disclosure may include at least one or more of the aforementioned components, omit some of them, or further include other additional components. Operations performed by modules, programming modules or other components in accordance with various embodiments of the present disclosure may be carried out sequentially, simultaneously, repeatedly, or heuristically. Furthermore, some of the operations may be performed in a different order, or omitted, or include other additional operation(s).

According to an embodiment of the present disclosure, there is provided a storage medium storing commands, the commands configured to be executed by at least one processor of an electronic device to enable the at least one processor to perform at least one operation. The at least one operation may include storing a group including information related to at least one external electronic device related to an external body information obtaining device, receiving body information obtained by the external body information obtaining device from one of the at least one external electronic device in the group, determining an external electronic device corresponding to the received body information among the at least one external electronic device based on the received body information and the information related to the at least one external electronic device, and transmitting the received body information to the determined external electronic device.

As is apparent from the foregoing description, according to the embodiments of the present disclosure, when multiple users share a communication-capable body information obtaining device, body information obtained by the body information obtaining device may be provided to an electronic device corresponding to the detected body information even without establishing a communication link with the body information obtaining device. Thus, the user may be freed from the hassle of reconnection to the body information obtaining device or concerns about information leaks or exposure to others.

Various parameters of body information detected by the body information obtaining device may be used to distinguish between different pieces of body information. This way may present increased accuracy in determining which one of a plurality of electronic devices corresponds to the detected body information.

The embodiments disclosed herein are proposed for description and understanding of the disclosed technology and does not limit the present disclosure. Accordingly, the present disclosure should be interpreted as including all changes or various embodiments based on the present disclosure.

The control unit or processor may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. In addition, an artisan understands and appreciates that a "processor" or "microprocessor" may be hardware in the claimed disclosure. The control unit may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc.

What is claimed is:

1. An electronic device, comprising:
    a communication circuit;
    a memory storing identifiers for a plurality of external electronic devices included in a first group, including biometric information for a plurality of users associated respectively with the plurality of external electronic devices; and
    a processor configured to:
        receive biometric information detected by an external biometric detection device wherein the received biometric information does not include identification of a user to whom the received biometric information belongs,
        select a particular external electronic device from among the plurality of external electronic devices associated respectively with the plurality of users, based on the received biometric information and stored biometric information associated with the plurality of external electronic devices, wherein the particular external device belongs to a particular user, and
        transmit the received biometric information to the selected particular external electronic device belonging to the particular user,
    wherein the processor is configured to select the particular external electronic device by calculating a plurality of similarity scores respectively for the plurality of external electronic devices based on comparing the received biometric information to the stored biometric information, the plurality of similarity scores representing respective deviations of the stored biometric information with the received biometric information, and
    selecting the particular external electronic device having a similarity score indicating a lowest deviation with the received biometric information from among the plurality of external electronic devices,
    wherein the similarity score comprises a distance-based similarity score, and
    the particular external electronic device is selected as previously stored biometric information stored in the particular external electronic device has a lowest similarity score with the received biometric information from among the group,
    wherein the distance-based similarity score comprises an Euclidean distance-based similarity score.

2. The electronic device of claim 1, wherein the processor is configured to:
    transmit an instruction to the selected particular external electronic device to store the received biometric information.

3. The electronic device of claim 1, wherein the processor is configured to:
    in response to receiving a request for information related to the plurality of external electronic devices in the group from another external electronic device in the group different than the particular external electronic device, transmit the information related to the plurality of external electronic devices to the another external electronic device.

4. A non-transitory storage medium storing commands executable by a processor of an electronic device to cause the processor to:
    store in a memory identifiers for a plurality of external electronic devices included in a first group, including biometric information for a plurality of users associated respectively with the plurality of external electronic devices;
    receive biometric information detected by an external biometric detection device wherein the received biometric information does not include identification of a user to whom the received biometric information belongs; select a particular external electronic device from among the plurality of external electronic devices associated respectively with the plurality of users, based on the received biometric information and stored biometric information associated with the plurality of external electronic devices, wherein the particular external device belongs to a particular user; and
    transmit the received biometric information to the selected particular external electronic device belonging to the particular user,
    wherein the particular external electronic device is selected by:
    calculating a plurality of similarity scores respectively for the plurality external electronic devices based on comparing the received biometric information to the stored biometric information, the plurality of similarity scores representing respective deviations of the stored biometric information with the received biometric information, and selecting the particular external electronic device having a similarity score indicating a lowest deviation with the received biometric information from among the plurality of external electronic devices, wherein the similarity score comprises a distance-based similarity score, and the particular external electronic device is selected as previously stored biometric information stored in the particular external electronic device has a lowest similarity score with the received biometric information from among the group, wherein the distance-based similarity score comprises an Euclidean distance-based similarity score.

5. The non-transitory storage medium of claim 4, wherein the commands further include:

transmitting an instruction to the selected particular external electronic device to store the received biometric information.

6. The non-transitory storage medium of claim 4, wherein the commands further include:

in response to receiving a request for information related to the plurality of external electronic devices in the group from another external electronic device in the group different than the particular external electronic device, transmitting the information related to the one for more external electronic devices to the another external electronic device.

* * * * *